US012740977B2

(12) United States Patent
Schneider-Kramann

(10) Patent No.: US 12,740,977 B2
(45) Date of Patent: Sep. 22, 2026

(54) S100 PROTEINS AS NOVEL THERAPEUTIC TARGETS IN MYELOPROLIFERATIVE NEOPLASMS

(71) Applicant: ERASMUS UNIVERSITY MEDICAL CENTER ROTTERDAM, Rotterdam (NL)

(72) Inventor: Rebekka Katharina Marita Schneider-Kramann, Rotterdam (NL)

(73) Assignee: ERASMUS UNIVERSITY MEDICAL CENTER ROTTERDAM, Rotterdam (NL)

( * ) Notice: Subject to any disclaimer, the term of this patent is extended or adjusted under 35 U.S.C. 154(b) by 745 days.

(21) Appl. No.: 18/017,078

(22) PCT Filed: Jul. 23, 2021

(86) PCT No.: PCT/EP2021/070629

§ 371 (c)(1),
(2) Date: Jan. 19, 2023

(87) PCT Pub. No.: WO2022/018240

PCT Pub. Date: Jan. 27, 2022

(65) Prior Publication Data

US 2023/0293512 A1 Sep. 21, 2023

(30) Foreign Application Priority Data

Jul. 23, 2020 (EP) .................................... 20187323

(51) Int. Cl.

| | |
|---|---|
| ***A61K 31/4704*** | (2006.01) |
| ***A61K 45/06*** | (2006.01) |
| ***A61P 35/00*** | (2006.01) |

(52) U.S. Cl.

CPC .......... *A61K 31/4704* (2013.01); *A61K 45/06* (2013.01)

(58) Field of Classification Search

CPC ............................ A61K 31/4704; A61K 45/06

See application file for complete search history.

(56) References Cited

U.S. PATENT DOCUMENTS

| | | |
|---|---|---|
| 4,816,567 A | 3/1989 | Cabilly et al. |
| 5,641,870 A | 6/1997 | Rinderknecht et al. |
| 2010/0021472 A1 | 1/2010 | Srikrishna et al. |

FOREIGN PATENT DOCUMENTS

| | | |
|---|---|---|
| WO | WO 99/55678 A1 | 11/1999 |
| WO | WO 00/03991 A1 | 1/2000 |

(Continued)

OTHER PUBLICATIONS

BjÃ¶rk, P. et al. PLOS Biology. 2009, 7(4), e1000097. (Year: 2009).*

(Continued)

*Primary Examiner* — Clinton A Brooks
*Assistant Examiner* — Kendall Nicole Heitmeier
(74) *Attorney, Agent, or Firm* — James S. Keddie; Bozicevic, Field & Francis LLP

(57) ABSTRACT

The current invention pertains to an inhibitor of a S100 protein, preferably an inhibitor of a S100A8 or S100A9 protein, for the prevention or treatment of a myeloproliferative neoplasm. In particular, the invention pertains to an inhibitor of a S100A8 or S100A9 protein, for the prevention or treatment of primary myelofibrosis. The invention further pertains to a diagnostic method for identifying a subject suffering from a myeloproliferative neoplasm, comprising a step of detecting the presence of a S100 protein, preferably S100A8 or S100A9, in a biological sample.

13 Claims, 12 Drawing Sheets

Figure 1A:
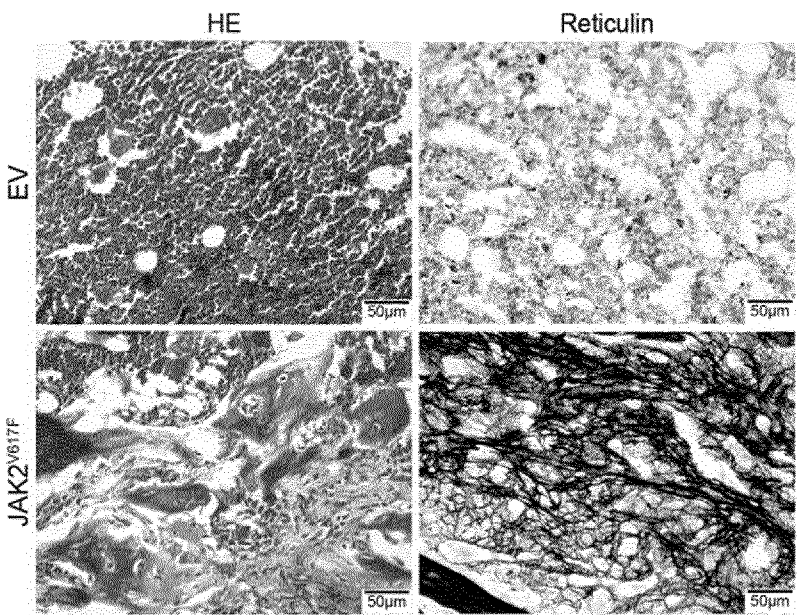
Figure 1B:
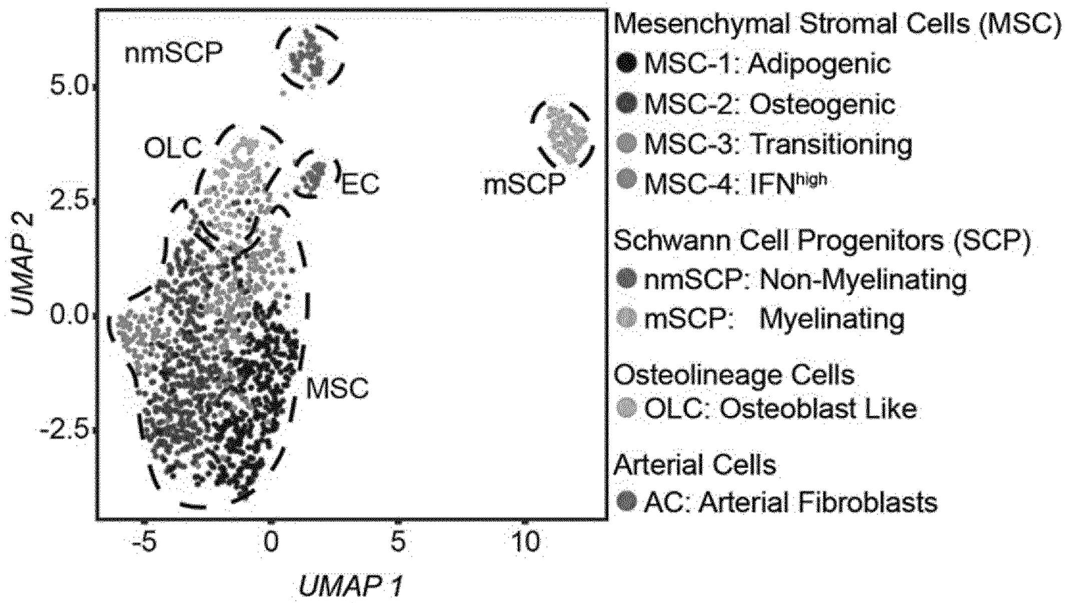

Mesenchymal Stromal Cells (MSC)
MSC-1: Adipogenic
MSC-2: Osteogenic
MSC-3: Transitioning
MSC-4: IFN^high
Schwann Cell Progenitors (SCP)
nmSCP: Non-Myelinating
mSCP: Myelinating
Osteolineage Cells
OLC: Osteoblast Like
Arterial Cells
AC: Arterial Fibroblasts

(56) References Cited

FOREIGN PATENT DOCUMENTS

| | | | | |
|---|---|---|---|---|
| WO | WO 03/106424 A1 | | 12/2003 | |
| WO | WO 2005/074899 A2 | | 8/2005 | |
| WO | WO 2012/004338 A1 | | 1/2012 | |
| WO | WO 2012/175541 A1 | | 12/2012 | |
| WO | WO 2016/042112 A1 | | 3/2016 | |
| WO | WO 2016/067238 A1 | | 5/2016 | |
| WO | WO 2016/078921 A1 | | 5/2016 | |
| WO | WO 2017/008153 A1 | | 1/2017 | |
| WO | WO-2017201491 A1 | * | 11/2017 | .............. A61P 19/04 |

OTHER PUBLICATIONS

KÃ¤llberg, E. et al. PLOS One. 2012, 7(3), e34207 (Year: 2012).*

Li et al., "Ruxolitinib-based combinations in the treatment of myelofibrosis: worth looking forward to", Annals of Hematology, 2020, 99: 1161-1176.

Altschul et al., "Basic Local Alignment Search Tool", J. Mol. Biol., 1990, 215: 403-410.

Altschul et al., "Gapped BLAST and PSI-BLAST: a new generation of protein database search programs", Nucleic Acids Research, 1997, 25(17): 3389-3402.

Barbui et al., "Philadelphia chromosome-negative classical myeloproliferative neoplasms: revised management recommendations from European LeukemiaNet", Leukemia., 2018, 32(5): 1057-1069.

Baryawno et al., "A Cellular Taxonomy of the Bone Marrow Stroma in Homeostasis and Leukemia", Cell, 2019, 177: 1915-1932.

Butler et al., "Integrating single-cell transcriptomic data across different conditions, technologies, and species", Nature Biotechnology, 2018, 36(5): 411-427.

Dar et al., "siRNAmod: A database of experimentally validated chemically modified siRNAs", Scientific Reports, 2016, 6:20031: pp. 1-8.

Decker et al., "Rare, protein-truncating variants in Atm, CHEK2 and PALB2, but not XRCC2, are associated with Increased breast cancer risks", J Med Genet, 2017, 54: 732-741.

Denmeade et al., "Bipolar AndrogenTherapy: The Rationale for Rapid Cycling of Supraphysiologic Androgen/Ablation in Men With Castration Resistant Prostate Cancer", Prostate., 2010, 70(14): 1600-1607.

Diklic et al., "The S100 Proteins as Mediators of Inflammation are Increased in Myeloproliferative Neoplasm and Downregulated By JAK2 Inhibition", Haematologica, 2016, 101 (s1), p. 806.

Diklic et al., "IL6 inhibition of inflammatory S100A8/9 proteins is NF-κB mediated in essential thrombocythemia", Cell Biochemistry & Function, 2020, 38: 362-372.

El Agha et al., "Mesenchymal Stem Cells in Fibrotic Disease", Cell Stem Cell, 2017, 21: 166-177.

Henikoff et al., "Amino acid substitution matrices from protein blocks", Proc. Natl. Acad. Sci., 1992, 89: 10915-10919.

Hiratsuka et al., "Tumour-mediated upregulation of chemoattractants and recruitment of myeloid cells predetermines lung metastasis", Nature Cell Biology, 2006, 8(12): 1369-1375, Supplementary Information 1-5, Supplementary Methods (2 pages).

Kawamoto et al., "TAK-242 selectively suppresses Toll-like receptor 4-signaling mediated by the intracellular domain", European Journal of Pharmacology, 2008, 584: 40-48.

Kovacic et al., "TLR4 and RAGE conversely mediate pro-inflammatory S100A8/9-mediated inhibition of proliferation- inked signaling in myeloproliferative neoplasms", Ceiiuiar Oncology, 2018, 41: 541-553.

Leimkuhler et al., "Heterogeneous bone-marrow stromal progenitors drive myelofibrosis via a druggable alarmin axis", Cell Stem Cell, Apr. 1, 2021, 28: 637-652.

Li et al., "A Novel Cyclohexene Derivative, Ethyl (6R)-6-[N-(2-Chloro-4-fluorophenyl)sulfamoyl]cyclohex-1-ene-1-carboxylate (TAK-242), Selectively Inhibits Toll-Like Receptor 4-Mediated Cytokine Production through Suppression of Intracellular Signaling", Molecular Pharmacology, 2006, 69: 1288-1295.

McCarthy et al., "Differential expression analysis of multifactor RNA-Seq experiments with respect to biological variation", Nucleic Acids Research, 2012, 40(10): 4288-4297.

Morrison et al., "Chimeric human antibody molecules: Mouse antigen-binding domains with human constant region domains", Proc. Nati. Acad. Sci., 1984, 81: 6851-6855.

Mullally et al., "Myeloproliferative Neoplasm Animal Models", Hematol Oncol Clin North Am., 2012, 26(5): 1065-1081.

Rampal et al., "Genomic and functional analysis of leukemic transformation of myeloproliferative neoplasms", PNAS, 2014, E5401-E5410.

Ribezzo et al., "Rps14, Csnk1a1 and miRNA145/miRNA146a deficiency cooperate in the clinical phenotype and activation of the innate immune system in the 5q-syndrome", Leukemia, 2019, 33: 1759-1772.

Ron et al., "Erodible Systems" in Treatise on Controlled Drug Delivery—A. Kydonieus Ed.—Marcel Dekker Inc.—New York, 1992, pp. 199-224.

Satija et al., "Spatial reconstruction of single-cell gene expression data", Nature Biotechnology, 2015, 33(5):495-502.

Schelbergen et al., "Prophylactic treatment with S100A9 inhibitor paquinimod reduces pathology in experimental collagenase-induced osteoarthritis", Ann Rheum Dis, 2015, 74:2254-2258.

Schneider et al., "Gli1+ Mesenchymal Stromal Cells are a Key Driver of Bone Marrow Fibrosis and an Important Cellular Therapeutic Target", Cell Stem Cell, 2017, 20: 785-800.

Stewart et al., "BET Inhibition Suppresses S100A8 and S100A9 Expression in Acute Myeloid Leukemia Cells and Synergises with Daunorubicin in Causing Cell Death", Hindawi, Bone Marrow Research, 2018, vol. 2018, Article ID 5742954, 9 pages.

Subramanian et al., "Gene set enrichment analysis: A knowledge-based approach for interpreting genome-wide expression profiles", PNAS, 2005, 102(43): 15545-15550.

Tikhonova et al., "The bone marrow microenvironment at single-cell resolution", Nature, 2019, 569: 222-249.

Vainchenker et al., "New mutations and pathogenesis of myeloproliferative neoplasms", Blood, 2011, 118(7): 1723-1735.

Vogl et al., "Autoinhibitory regulation of S100A8/S100A9 alarmin activity locally restricts sterile inflammation", J Clin Invest., 2018, 128(5): 1852-1866.

Wang et al., "S100A8/A9 in Inflammation", Frontiers in Immunology, 2018, vol. 9, Article 1298, pp. 1-14.

Yu et al., "clusterProfiler: an R Package for Comparing Biological Themes Among Gene Clusters", OMICS A Journal of Integrative Biology, 2012, 16(5): 284-287.

Zapata et al., "Engineering linear F(ab')2 fragments for efficient production in *Escherichia coli* and enhanced antiproliferative activity", Protein Engineering, 1995, 8(10): 1057-1062.

* cited by examiner

HE

S100 PROTEINS AS NOVEL THERAPEUTIC TARGETS IN MYELOPROLIFERATIVE NEOPLASMS

CROSS-REFERENCE TO RELATED APPLICATIONS

This application is a § 371 national phase of International Application No. PCT/EP2021/070629, filed on Jul. 23, 2021, which claims the benefit of European Application No. 20187323.9, filed on Jul. 23, 2020, which applications are incorporated by reference herein.

FIELD OF THE INVENTION

The present invention relates to the field of medicine, in particular to molecular oncology. More specifically, the invention concerns an inhibitor for use in the prevention, amelioration and/or treatment of a myeloproliferative neoplasm, preferably a myeloproliferative neoplasm associated with a fibrotic phase. The invention further concerns a novel biomarker for a myeloproliferative neoplasm. The novel biomarker may determine the severity or phase of a myeloproliferative neoplasm and/or can be used to determine (stratify) whether a subject suffering from a myeloproliferative neoplasm may benefit from an S100 protein inhibitor as defined herein.

BACKGROUND

Myeloproliferative neoplasms (MPNs), or myeloproliferative diseases (MPDs), are a group of diseases of the bone marrow in which excess cells are produced. MPNs arise from precursors of the myeloid lineages in the bone marrow, and may encompass bone marrow fibrosis. Bone marrow (BM) fibrosis is characterized by continuous replacement of blood-forming cells in the bone marrow by excessive scar tissue. Primary myelofibrosis (PMF) is the prototypic example of progressive development of BM fibrosis. The hallmark feature of overt PMF is the excess deposition of extracellular matrix (ECM) which is accompanied by a progressive loss of hematopoiesis (cytopenia) causing transfusion dependency, splenomegaly due to extramedullary hematopoiesis and ultimately bone marrow failure. Currently the only available and potentially curative treatment of MPN with fibrosis is bone marrow transplantation. However, bone marrow transplantation is a complex treatment carrying a significant risk of serious complications. In addition, a majority of patients is not eligible for this challenging procedure e.g. due to age, disease stage, comorbidities and the lack of a suitable donor.

Although the molecular alterations in hematopoietic cells which drive the development of myeloproliferative neoplasms (MPN) have been largely defined (Vainchenker et al., 2011; Rampal et al., 2014), reactive cellular alterations in the non-hematopoietic compartment remain rather obscure and have not been studied at single cell level.

The bone marrow morphology in patients with PMF suggests that there is a stepwise evolution from an initial pre-fibrotic phase with absent to minimal fibrosis, to a fibrotic phase with marked reticulin or collagen fibrosis, and often accompanied by osteosclerosis. However, the initial changes and sequential events underlying the pre-fibrotic phase of the disease are not well characterized (Barbui et al., 2018).

The plethora of stromal cells in a normal, healthy HSC niche (Baryawno et al., 2019; Tikhonova et al., 2019) suggests that different stromal subtypes not only have distinct roles in normal hematopoiesis but also in bone marrow fibrosis, including PMF. In solid organ fibrosis, mesenchymal stromal cells (MSCs), which in this context are also often referred to as MSClike cells, are thought to be a major cellular source for fibrosis-driving cells (El Agha et al., 2017). These findings are mainly derived from genetic fate tracing experiments which allow to study the cell fate in response to a pathological stimulus. The well accepted hypothesis in solid organ fibrosis is that in the presence of fibrosis-inducing insults, such as exposure to proinflammatory and pro-fibrotic cytokines, affects MSCs/MSC-like cells and leads to a fate switch towards myofibroblasts, which in turn drives fibrosis by depositing ECM.

One major open question in solid organ fibrosis is if MSCs are a distinct or heterogeneous cell population. In the bone marrow, it has been demonstrated that MSCs contribute to fibrosis-driving α-SMA+ myofibroblasts (Decker et al., 2017; Schneider et al., 2017) but it has remained unknown if they are the only source of fibrosis-driving cells in the bone marrow microenvironment or if other cell types of the non-hematopoietic bone marrow niche contribute to the fibrotic transformation.

There is still a need in the art for an effective and/or earlier treatment of myeloproliferative neoplasms, in particular for the treatment of primary myelofibrosis. In addition, there is a need in the art for a biomarker indicative of a myeloproliferative neoplasm.

SUMMARY

The invention may be summarized in the following embodiments:

Embodiment 1. An inhibitor of an S100 protein for use in the prevention or treatment of a myeloproliferative neoplasm associated with a fibrotic phase, wherein the myeloproliferative neoplasm is preferably at least one of primary myelofibrosis, essential thrombocythemia and polycythemia vera.

Embodiment 2. An inhibitor for use according to embodiment 1, wherein the myeloproliferative neoplasm is primary myelofibrosis.

Embodiment 3. An inhibitor for use according to embodiment 1 or 2, wherein the S100 protein is at least one of S100A8 and S100A9.

Embodiment 4. An inhibitor for use according to any one of the preceding embodiments, wherein the inhibitor is at least one of:

i) an inhibitor that prevents or reduces expression of the S100 protein in a cell; and ii) an inhibitor that inhibits S100 protein functional activity.

Embodiment 5. An inhibitor for use according to any one of the preceding embodiments, wherein the inhibitor is a small non-coding RNA or a small molecule.

Embodiment 6. An inhibitor for use according to embodiment 5, wherein the inhibitor is a small molecule of formula (I)

(I)

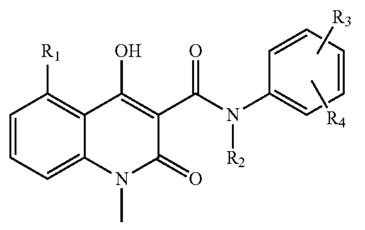

or a pharmaceutically acceptable salt thereof,
wherein

- $R_1$ is selected from the group consisting of H, methyl, ethyl, n-propyl, iso-propyl, methoxy, ethoxy, fluoro, chloro, bromo, trifluoromethyl, and trifluoromethoxy;
- $R_2$ is C1-C4 alkyl;
- $R_3$ is selected from the group consisting of methyl, methoxy, hydrogen, fluoro, chloro, bromo, trifluoromethyl, and trifluoromethoxy; and
- $R_4$ is selected from the group consisting of hydrogen, fluoro and chloro, with the proviso that $R_4$ is selected from fluoro and chloro only when $R_3$ is selected from fluoro and chloro.

Embodiment 7. An inhibitor for use according to embodiment 6, wherein $R_2$ is methyl or ethyl.

Embodiment 8. An inhibitor for use according to embodiment 6 or 7, wherein $R_3$ is in para-position and is selected from the group consisting of methyl, methoxy, fluoro, chloro, trifluoromethyl, and trifluoromethoxy.

Embodiment 9. An inhibitor for use according to any one of embodiments 6-8, wherein $R_4$ is H.

Embodiment 10. An inhibitor for use according to any one of embodiments 6-9, wherein the inhibitor is 4-hydroxy-5-methoxy-N,I-dimethyl-2-oxo-N-[4-(trifluoromethyl)phenyl]-1,2-dihydroquinoline-3-carboxamide (tasquinimod).

Embodiment 11. An inhibitor for use according to any one of the preceding embodiments, wherein the prevention or treatment is by administration of the inhibitor at a total daily dose of about 0.05-10 mg.

Embodiment 12. An inhibitor for use according to any one of the preceding embodiments, wherein the prevention or treatment is by oral administration of the inhibitor.

Embodiment 13. An inhibitor for use according to any one of the preceding embodiments, wherein the prevention or treatment further comprises at least one of radiation therapy, chemotherapy, and stem cell transplantation.

Embodiment 14. An agent for identifying a subject suffering from a myeloproliferative neoplasm, wherein the agent binds to an S100 protein, preferably an S100A8 or S100A9 protein, and wherein the agent further comprises a detectable label, wherein preferably the agent is a small molecule, an antibody or an antigen-binding fragment thereof.

Embodiment 15. An agent according to embodiment 14, wherein the agent is tasquinimod, preferably deuterium-enriched tasquinimod.

Embodiment 16. A method for identifying a subject suffering from a myeloproliferative neoplasm, comprising a step of detecting the presence of an S100 protein, preferably S100A8 or S100A9, in a biological sample, wherein the method is preferably an ex vivo method.

Embodiment 17. A method according to embodiment 16, wherein the presence of the S100 protein is detected by exposing the biological sample to the agent of embodiment 14 or 15.

Embodiment 18. A method according to embodiments 16 or 17, wherein the biological sample is a blood sample or a bone marrow sample.

Embodiment 19. A method according to any one of embodiments 16-18, wherein the myeloproliferative neoplasm is primary myelofibrosis.

Embodiment 20. A method according to embodiment 19, wherein the method identifies a subject suffering from Grade 0, 1, 2 or 3 primary myelofibrosis.

Definitions

Various terms relating to the methods, compositions, formulations, uses and other aspects of the present invention are used throughout the specification and claims. Such terms are to be given their ordinary meaning in the art to which the invention pertains, unless otherwise indicated. Other specifically defined terms are to be construed in a manner consistent with the definition provided herein. Although any methods and materials similar or equivalent to those described herein can be used in the practice for testing of the present invention, the preferred materials and methods are described herein.

Methods of carrying out the conventional techniques used in methods of the invention will be evident to the skilled worker. The practice of conventional techniques in molecular biology, biochemistry, computational chemistry, cell culture, recombinant DNA, bioinformatics, genomics, sequencing and related fields are well-known to those of skill in the art and are discussed, for example, in the following literature references: Sambrook et al., Molecular Cloning. A Laboratory Manual, 2nd Edition, Cold Spring Harbor Laboratory Press, Cold Spring Harbor, N. Y., 1989; Ausubel et al., Current Protocols in Molecular Biology, John Wiley & Sons, New York, 1987 and periodic updates; and the series Methods in Enzymology, Academic Press, San Diego.

"A," "an," and "the": these singular form terms include plural referents unless the content clearly dictates otherwise. The indefinite article "a" or "an" thus usually means "at least one". Thus, for example, reference to "a cell" includes a combination of two or more cells, and the like.

"About" and "approximately": these terms, when referring to a measurable value such as an amount, a temporal duration, and the like, is meant to encompass variations of ±20% or ±10%, more preferably ±5%, even more preferably 1%, and still more preferably ±0.1% from the specified value, as such variations are appropriate to perform the disclosed methods. Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

"And/or": The term "and/or" refers to a situation wherein one or more of the stated cases may occur, alone or in combination with at least one of the stated cases, up to with all of the stated cases.

As used herein, with "at least" a particular value means that particular value or more. For example, "at least 2" is understood to be the same as "2 or more" i.e., 2, 3, 4, 5, 6, 7, 8, 9, 10, 11, 12, 13, 14, 15, . . . , etc.

"Comprising": this term is construed as being inclusive and open ended, and not exclusive. Specifically, the term and variations thereof mean the specified features, steps or components are included. These terms are not to be interpreted to exclude the presence of other features, steps or components.

Exemplary: this terms means "serving as an example, instance, or illustration," and should not be construed as excluding other configurations disclosed herein.

As used herein "cancer" and "cancerous", refer to or describe the physiological condition in mammals that is typically characterized by unregulated cell growth. Cancer is also referred to as malignant neoplasm. A preferred cancer is a blood cancer, preferably the blood cancer is a myoloproliferative neoplasm.

As used herein, "in combination with" is intended to refer to all forms of administration that provide a first drug together with a further (second, third) drug. The drugs may be administered simultaneous, separate or sequential and in any order. Drugs administered in combination have biological activity in the subject to which the drugs are delivered.

As used herein "simultaneous" administration refers to administration of more than one drug at the same time, but not necessarily via the same route of administration or in the form of one combined formulation. For example, one drug may be provided orally whereas the other drug may be provided intravenously. Separate includes the administration of the drugs in separate form and/or at separate moments in time, but again, not necessarily via the same route of administration. Sequentially indicates that the administration of a first drug is followed, immediately or in time, by the administration of the second drug.

A used herein "compositions", "products" or "combinations" useful in the methods of the present disclosure include those suitable for various routes of administration, including, but not limited to, intravenous, subcutaneous, intradermal, subdermal, intranodal, intratumoral, intramuscular, intraperitoneal, oral, nasal, topical (including buccal and sublingual), rectal, vaginal, aerosol and/or parenteral or mucosal application. The compositions, formulations, and products according to the disclosure invention normally comprise the drugs (alone or in combination) and one or more suitable pharmaceutically acceptable excipients.

As used in the context of the invention, the terms "prevent", "preventing", and "prevention" refers to the prevention or reduction of the recurrence, onset, development or progression of a disease, preferably a myeloproliferative neoplasm as defined herein, or the prevention or reduction of the severity and/or duration of the disease or one or more symptoms thereof.

As used herein, the terms "treat", "treating" and "treatment" refer to the reduction or amelioration of the progression, severity, and/or duration of a disease, preferably a myeloproliferative neoplasm as defined herein, and/or reduces or ameliorates one or more symptoms of the disease.

As used in the context of the invention, the terms "therapies" and "therapy" can refer to any protocol(s), method(s) and/or agent(s), preferably as specified herein below, that can be used in the prevention, treatment, management or amelioration of a disease, preferably a myeloproliferative neoplasm as defined herein below, or one or more symptoms thereof.

As used herein, the term "effective amount" refers to the amount of an agent, e.g., of an inhibitor as defined herein, which is sufficient to reduce the severity, and/or duration of a myeloproliferative neoplasm, ameliorate one or more symptoms thereof, prevent the advancement of the myeloproliferative neoplasm, or cause regression of the myeloproliferative neoplasm, or which is sufficient to result in the prevention of the development, recurrence, onset, or progression of the myeloproliferative neoplasm or one or more symptoms thereof. Alternatively or in addition, the effective amount of the inhibitor can be an amount that enhances or improves the prophylactic and/or therapeutic effect(s) of another therapy. Preferably, the effective amount of the inhibitor as defined herein prevents the onset, reduces and/or reverses the progression of primary myelofibrosis in a subject in need thereof. Preferably, the effective amount of the inhibitor as defined herein prevents the onset of primary myelofibrosis in a subject in need thereof. Preferably, the effective amount of the inhibitor as defined herein reduces the progression of primary myelofibrosis in a subject in need thereof. Preferably, the effective amount of the inhibitor as defined herein reverses the progression of primary myelofibrosis in a subject in need thereof.

Preferably, the effective amount of the inhibitor as defined herein prevents the onset, reduces and/or reverses the progression of primary myelofibrosis in a subject having a myeloproliferative neoplasm. Preferably, the effective amount of the inhibitor as defined herein prevents the onset of primary myelofibrosis in a subject having a myeloproliferative neoplasm. Preferably, the effective amount of the inhibitor as defined herein reduces the progression of primary myelofibrosis in a subject having a myeloproliferative neoplasm. Preferably, the effective amount of the inhibitor as defined herein reverses the progression of primary myelofibrosis in a subject having a myeloproliferative neoplasm.

The effective amount of the inhibitor used to practice the present invention for therapeutic treatment of a myeloproliferative neoplasm may vary depending upon the manner of administration, the age, body weight, and general health of the subject. Ultimately, the attending physician or veterinarian will decide the appropriate amount and dosage regimen. Such amount is referred to as an "effective" amount. Thus, in connection with the administration of an inhibitor which, in the context of the current disclosure, is "effective against" a myeloproliferative neoplasm indicates that administration in a clinically appropriate manner results in a beneficial effect for at least a statistically significant fraction of patients, such as an improvement of symptoms, a cure, a reduction in at least one disease sign or symptom, extension of life, improvement in quality of life, or other effect generally recognized as positive by medical doctors familiar with treating the particular type of disease or condition.

The inhibitor of the as detailed herein is preferably an (active) agent. The term "agent" refers generally to any entity which is normally not present or not present at the levels being administered to a cell, tissue or subject. An agent can be a compound or a composition. An agent can e.g. be selected from the group consisting of: polynucleotides, polypeptides, small molecules, antibodies and functional fragments thereof.

The medical use herein described is formulated as a compound as defined herein for use as a medicament for treatment of the stated disease(s) but could equally be formulated as a method of treatment of the stated disease(s) using a compound as defined herein, a compound as defined herein for use in the preparation of a medicament to treat the stated disease(s), and use of a compound as defined herein for the treatment of the stated disease(s) by administering an effective amount. Such medical uses are all envisaged by the present invention.

As used herein, the term "small molecule" can refer to compounds that are "natural product-like," but mostly will refer synthetic compounds. A small molecule is typically characterized in that it contains several carbon-carbon bonds, and has a molecular weight of less than 5000 Daltons (5 kD), preferably less than 3 kD, still more preferably less than 2 kD, and most preferably less than 1 kD. In some cases it is preferred that a small molecule have a molecular mass equal to or less than 700 Daltons.

The term "protein" or "polypeptide" refers to a molecule consisting of a chain of amino acids, without reference to a specific mode of action, size, 3 dimensional structure or origin. A "fragment" or "portion" of a protein may thus still be referred to as a "protein." A protein as defined herein and as used in any method as defined herein may be an isolated protein. An "isolated protein" is used to refer to a protein which is no longer in its natural environment, for example in vitro or in a recombinant bacterial or animal host cell. Preferably, the protein comprises more than 50 amino acid residues.

The term "proteinaceous molecule" is herein understood as a molecule comprising a short chain of amino acid monomers linked by peptide (amide) bonds. The short chain of amino acid monomers comprise 2 or more amino acid residues. Preferably, the chain of amino acids has at least 2, 3, 4, 5, 6, 7, 8, 9, 10, 11, 12, 13, 14, 15 amino acid residues. Preferably, the there are no more than 100 amino acid residues. Preferably, there are no more than 50 amino acid residues in the proteinaceous molecule. Preferably, the proteinaceous molecule has about 2-100, 3-50, 4-40 or 5-30, or 6-20 amino acid residues. Preferably, the proteinaceous molecule has 2, 3, 4, 5, 6, 7, 8, 9, 10, 11, 12, 13, 14 or 15 amino acid residues. Optionally, the proteinaceous molecule comprises one or more additional organic moieties, such as, but not limited to a linking moiety to generate a cyclised proteinaceous molecule.

An "aptamer" preferably is a nucleic acid molecule having a particular nucleotide sequence. An aptamer can include any suitable number of nucleotides. An aptamer may comprise RNA or DNA, or comprises both ribonucleotide residues and deoxyribonucleotide residues. An aptamer may be single stranded, double stranded, or contain double stranded or triple stranded regions. In addition, an aptamer may comprise chemical modified residues, e.g. to improve its stability. An aptamer will typically be between about 10 and about 300 nucleotides in length. More commonly, an aptamer will be between about 30 and about 100 nucleotides in length. Aptamers to a given target (i.e. an S100 protein as defined herein) include nucleic acids that may be identified from a candidate mixture of nucleic acids using a method comprising the steps of: (a) contacting the candidate mixture with the target, wherein nucleic acids having an increased affinity to the target relative to other nucleic acids in the candidate mixture can be partitioned from the remainder of the candidate mixture; (b) partitioning the increased affinity nucleic acids from the remainder of the candidate mixture; and (c) amplifying the increased affinity nucleic acids to yield an enriched mixture of nucleic acids, whereby aptamers of the target molecule are identified.

It is recognized that affinity interactions are a matter of degree; however, in this context, the "specific binding affinity" of an aptamer for its target means that the aptamer binds to its target generally with a much higher degree of affinity than it binds to other, non-target, components in a mixture or sample.

The term "antibody" is used in the broadest sense and specifically covers, e.g. monoclonal antibodies, including agonists and antagonist, neutralizing antibodies, full length or intact monoclonal antibodies, polyclonal antibodies, multivalent antibodies, single chain antibodies and functional fragments of antibodies, including Fab, Fab', F(ab')2 and Fv fragments, diabodies, triabodies, single domain antibodies (sdAbs), heavy-chain antibodies, nanobodies, as long as they exhibit the desired biological and/or immunological activity. An antibody can be human and/or humanized. "Humanized" forms of non-human (e.g., rodent) antibodies are chimeric antibodies that contain minimal sequence derived from the non-human antibody.

An antibody "which binds" an antigen of interest, preferably to the S100 protein as defined herein, is one that binds said antigen with sufficient affinity such that the antibody is useful for the detection of an S100 protein, preferably the detection of an S100A8 or S100A9, as defined herein.

"Antibody fragments" comprise a portion of an intact antibody, preferably at least the antigen binding and/or variable region of the intact antibody. Examples of antibody fragments include Fab, Fab', $F(ab')_2$, and Fv fragments; diabodies; triabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments. In one embodiment, an antibody fragment comprises an antigen binding site of the intact antibody and thus retains the ability to bind the antigen.

The term "nanobody" is well-known in the art. A nanobody is an antibody fragment comprising or consisting of a $V_HH$ domain of a heavy chain only antibody. A preferred nanobody is derivable from the camelidae family, preferably derivable from a Llama.

The term "monoclonal antibody" as used herein refers to an antibody obtained from a population of substantially homogeneous antibodies, i.e., the individual antibodies comprising the population are identical except for possible naturally occurring mutations that may be present in minor amounts. The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc.), and human constant region sequences.

Preferably, the antibody for binding to the diagnostic marker as defined herein does not significantly cross-react with other proteins.

"Amino acid sequence": This refers to the order of amino acid residues of, or within a protein. In other words, any order of amino acids in a protein may be referred to as amino acid sequence.

"Nucleotide sequence": This refers to the order of nucleotides of, or within a nucleic acid. In other words, any order of nucleotides in a nucleic acid may be referred to as nucleotide sequence.

The terms "homology", "sequence identity" and the like are used interchangeably herein. Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide.

The term "complementarity" is herein defined as the sequence identity of a nucleotide sequence to a fully complementary strand (e.g. the second, or reverse, strand). For example, a sequence that is 100% complementary (or fully complementary) is herein understood as having 100% sequence identity with the complementary strand and e.g. a sequence that is 80% complementary is herein understood as having 80% sequence identity to the (fully) complementary strand.

"Identity" and "similarity" can be readily calculated by known methods. "Sequence identity" and "sequence similarity" can be determined by alignment of two peptide or two nucleotide sequences using global or local alignment algorithms, depending on the length of the two sequences. Sequences of similar lengths are preferably aligned using a global alignment algorithm (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, CA 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blosum62 for proteins and DNAFull for DNA). When sequences have a substantially different overall lengths, local alignments, such as those using the Smith Waterman algorithm, are preferred.

Alternatively, percentage similarity or identity may be determined by searching against public databases, using algorithms such as FASTA, BLAST, etc. Thus, the nucleic acid and protein sequences of the present invention can further be used as a "query sequence" to perform a search against public databases to, for example, identify other family members or related sequences. Such searches can be performed using the BLASTn and BLASTx programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the BLASTx program, score=50, word length=3 to obtain amino acid sequences homologous to protein molecules of the invention. To obtain gapped alignments for comparison purposes, Gapped BLAST can be utilized as described in Altschul et al., (1997) Nucleic Acids Res. 25 (17): 3389-3402. When utilizing BLAST and Gapped BLAST programs, the default parameters of the respective programs (e.g., BLASTx and BLASTn) can be used. See the homepage of the National Center for Biotechnology Information.

Nucleotide sequences of the invention may also be defined by their capability to hybridize with the specific nucleotide sequences disclosed herein or parts thereof, under moderate, or preferably under stringent hybridization conditions. Stringent hybridization conditions are herein defined as conditions that allow a nucleic acid sequence of at least about 25, preferably about 50 nucleotides, 75 or 100 and most preferably of about 200 or more nucleotides, to hybridize at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridization is performed overnight, i.e. at least for 10 hours and preferably washing is performed for at least one hour with at least two changes of the washing solution. These conditions will usually allow the specific hybridization of sequences having about 90% or more sequence identity.

Moderate conditions are herein defined as conditions that allow a nucleic acid sequences of at least 50 nucleotides, preferably of about 200 or more nucleotides, to hybridize at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridization is performed overnight, i.e. at least for 10 hours, and preferably washing is performed for at least one hour with at least two changes of the washing solution. These conditions will usually allow the specific hybridization of sequences having up to 50% sequence identity. The person skilled in the art will be able to modify these hybridization conditions in order to specifically identify sequences varying in identity between 50% and 90%.

Examples of pharmaceutically acceptable salts comprise salts with (as counter ion) an alkali metal ion, e.g. $Li^+$, $Na^+$ or $K^+$, or with an alkaline earth ion, e.g. $Mg^{++}$ or $Ca^{++}$, or with any other pharmaceutically acceptable metal ion, e.g. $Zn^{++}$ or $Al^{3+}$; or pharmaceutically acceptable salts formed with organic bases, such as diethanolamine, ethanolamine, N-methylglucamine, triethanolamine or tromethamine.

The term "C1-C4 alkyl" refers to a branched or unbranched alkyl group having from 1, 2, 3 or 4 carbon atoms, i.e. methyl, ethyl, n-propyl, isopropyl, n-butyl, sec-butyl, isobutyl or tertbutyl. The term methoxy refers to the moiety MeO—, or CH3O—. The term ethoxy refers to the moiety EtO—, or $CH_3CH_2O$—. The terms fluoro, chloro and bromo also may be represented by F, Cl and Br. The term trifluoromethyl refers to the moiety $CF_3$—. The term trifluoromethoxy refers to the moiety $CF_3O$—.

DETAILED DESCRIPTION

The inventors discovered that S100 proteins, and in particular the Alarmins S100A8 and S100A9, were upregulated in the blood cancer myeloproliferative neoplasms (MPN) in a murine model as well as in patient samples. Inhibiting the activity of S100A8 and S100A9 in an MPN mouse model strikingly improved disease associated symptoms and fibrosis.

The inventors discovered that inhibiting the activity of an S100 protein, in particular an S100A8/A9 protein, results in an effective and/or earlier treatment of myeloproliferative neoplasms, in particular the treatment of primary myelofibrosis. This novel treatment can prevent the progression of the myeloproliferative neoplasm, and/or reverses the disease. In addition, the treatment can be used in combination with another available treatment for a myeloproliferative neoplasm, in particular in combination with another treatment for primary myelofibrosis, preferably to target complementary pathways. The inventors further discovered that the S100 protein, preferably the S100A8/A9 protein, can function as a biomarker indicative of a myeloproliferative neoplasm, and may be used to stratify patients.

In a first aspect, the invention therefore pertains to an inhibitor of an S100 protein for use in the prevention or treatment of a myeloproliferative neoplasm. Preferably, the myeloproliferative neoplasm is associated with a fibrotic phase.

Preferably, the prevention or treatment as described herein is the prevention or treatment of a myeloproliferative neoplasm in a mammalian subject, preferably a human subject.

Myeloproliferative Neoplasm

A myeloproliferative neoplasm (MPN) is a type of blood cancer, characterized by the overproduction of at least one of red blood cells, white blood cells and platelets.

The MPN may be categorized by the presence or absence of the so-called Philadelphia chromosome, which is a genetic abnormality in chromosome 22. More in particular, the (Philadelphia) chromosome 22 comprises a reciprocal translocation, t(9;22)(q34;q11), of genetic material between chromosome 9 and chromosome 22, and contains the fusion gene BCR-ABL1. Preferably, the MPN is negative for the Philadelphia chromosome.

An MPN may be characterized by the presence, or development of, a fibrotic phase. Alternatively or in addition, the MPN is therefore preferably associated with a fibrotic phase. It is understood herein that the prevention or treatment as detailed herein can be before, during and/or after the onset of a fibrotic phase, preferably bone marrow fibrosis. The fibrotic phase is preferably characterized by at least one of collagenous fibrosis and reticulin fibrosis, preferably in the bone marrow. The MPN as defined herein preferably may result in, or is characterised by, an fibrotic phase, preferably a bone marrow fibrotic phase.

Alternatively or in addition, the MPN is preferably associated with a JAK2 mutation, preferably a JAK2 V617F mutation or a functional equivalent thereof, such as but not limited to, a JAK2 exon 12 mutation.

Preferably, the myeloproliferative neoplasm is selected from the group consisting of primary myelofibrosis, essential thrombocythemia, polycythemia vera, Chronic neutrophilic leukemia, chronic myelogenous leukemia, acute myelogenous leukemia, chronic eosinophilic leukemia and mastocytosis. Preferably, the myeloproliferative neoplasm is selected from the group consisting of primary myelofibrosis, essential thrombocythemia, polycythemia vera, Chronic neutrophilic leukemia, chronic eosinophilic leukemia and mastocytosis. Preferably, the myeloproliferative neoplasm is selected from the group consisting of primary myelofibrosis, essential thrombocythemia, and polycythemia vera. Essential thrombocythemia and polycythemia vera may develop into primary myelofibrosis.

Essential thrombocythemia (ET) is a chronic blood cancer (myeloproliferative neoplasm) characterised by the overproduction of platelets (thrombocytes) by megakaryocytes in the bone marrow. Essential thrombocythemia may develop into myelofibrosis.

Polycythemia vera is a myeloproliferative neoplasm in which the bone marrow makes too many red blood cells. It may also result in the overproduction of white blood cells and platelets. Polycythemia vera may develop into myelofibrosis.

Preferably, the myeloproliferative neoplasm is primary myelofibrosis. Primary myelofibrosis (also called myelofibrosis, chronic idiopathic myelofibrosis, or agnogenic myeloid metaplasia) is a disorder in which normal bone marrow tissue is gradually replaced with a fibrous scar-like material. Over time, this may lead to progressive bone marrow failure. Myelofibrosis can the advanced stage of the Philadelphia chromosome-negative myeloproliferative neoplasms (MPNs). Around one third of people with myelofibrosis have been previously diagnosed with polycythemia (post-polycythaemic myelofibrosis) or essential thrombocythaemia (post-ET myelofibrosis). In primary myelofibrosis, chemicals released by high numbers of platelets and abnormal megakaryocytes (platelet forming cells) may overstimulate the fibroblasts. This can result in the overgrowth of thick coarse fibres in the bone marrow, which gradually replace normal bone marrow tissue. Over time this may destroy the normal bone marrow environment, preventing the production of adequate numbers of red cells, white cells and platelets, i.e. resulting in cytopenia. This can result in anaemia, low platelet counts (summarized as cytopenia) and the production of blood cells in areas outside the bone marrow for example in the spleen and liver, which become enlarged as a result.

Administration of the inhibitor of the S100 protein to prevent or treat an MPN, preferably an MPN as defined herein, may prevent, normalize or reduce at least one symptom associated with the MPN. Preferably, administration of the inhibitor of the S100 protein to prevent or treat an MPN, preferably an MPN as defined herein, may prevent, normalize or reduce at least one symptom associated with an MPN-related bone marrow fibrosis. Preferably administration of the inhibitor of the S100 protein to prevent or treat an MPN, preferably an MPN as defined herein, may prevent, normalize or reduce at least one of leucocytosis, splenomegaly, platelet counts, thrombocytosis and fibrosis grade. Preferably administration of the inhibitor of the S100 protein to prevent or treat an MPN, preferably an MPN as defined herein, may reduce the grade of myelofibrosis.

Currently, there is no therapy available to reduce or prevent myelofibrosis in patients suffering from a MPN. The inventors have now discovered that using an inhibitor of S100A8/A9, MPN disease progression can be halted, in particular progression into fibrotic phase is prevented and even reversed.

Hence an inhibitor of an S100 protein, preferably an inhibitor of at least one of S100A8/A9, can be used for the prevention and/or reduction of myelofibrosis in a subject in need thereof, preferably for the prevention and/or reduction of myelofibrosis in a subject suffering from a MPN. In addition or alternatively, an inhibitor of an S100 protein, preferably an inhibitor of at least one of S100A8/A9, can be used to reduce grade 3 myelofibrosis to at least one of grade 2, grade 1, or grade 0 in a subject in need thereof, preferably in a subject suffering from an MPN. An inhibitor of an S100 protein, preferably an inhibitor of at least one of S100A8/A9, can be used to reduce grade 2 myelofibrosis to at least one of grade 1 or grade 0 in a subject in need thereof, preferably in a subject suffering from an MPN. An inhibitor of an S100 protein, preferably an inhibitor of at least one of S100A8/A9, can be used to reduce grade 1 myelofibrosis to grade 0 in a subject in need thereof, preferably in a subject suffering from an MPN.

S100 Protein

The inventors discovered that the inhibition of an S100 protein can be used for the prevention or treatment of a myeloproliferative neoplasm, preferably a myeloproliferative neoplasm as defined herein above. The S100 proteins are preferably a family of low-molecular-weight proteins characterized by two calcium-binding sites that have helix-loop-helix (ËF-hand type") conformation. There are at least 21 different S100 proteins and they are encoded by a family of genes whose symbols use the S100 prefix. They are considered Damage-associated molecular pattern molecules (DAMPs, also termed Alarmins). S100 proteins are localized in the cytoplasm and/or nucleus of a wide range of cells, and involved in the regulation of a number of cellular processes such as cell cycle progression and differentiation.

The S100 protein to be inhibited in accordance with the invention preferably is a mammalian S100 protein, more preferably a human S100 protein. The S100 protein to be inhibited is preferably selected from the group consisting of S100A1, S100A2, S100A3, S100A4, S100A5, S100A6, S100A7 (psoriasin), S100A8 (calgranulin A), S100A9 (calgranulin B), S100A10, S100A11, S100A12 (calgranulin C), S100A13, S100A14, S100A15 (koebnerisin), S100A16, S100B and S100P. More preferably the S100 protein to be inhibited is an S100A protein, of which at least one of S100A8 and S100A9 is preferred, of which S100A9 is most preferred. S100A8 and S100A9 form a heterodimer called calprotectin, which is secreted during inflammation. Other names for calprotectin include MRP8-MRP14, calgranulin A and B, cystic fibrosis antigen, L1, 60BB antigen, and 27E10 antigen. In an embodiment, the S100 protein to be inhibited in accordance with the invention is preferably the heterodimer calprotectin.

Inhibitor of an S100 Protein

An inhibitor of an S100 protein, preferably an inhibitor of at least one of S100A8 and S100A9, is herein defined as any agent that reduces or eliminates the activity, preferably the specific activity, of said S100 protein in a cell. Preferably, the activity of the S100 protein is reduced or eliminated in the cell by at least one of i) reducing or inhibiting the functional activity of the S100 protein in the cell, and
ii) reducing or inhibiting the expression of the S100 protein in the cell.

The inventors discovered that the inhibition of an S100 protein, in particular the inhibition of at least one of S100A8 or S100A9, can be used for the prevention or treatment of an MPN. The skilled person thus understands that invention is not limited to any specific inhibitor of an S100 protein, preferably is not limited to any specific inhibitor of an S100A8 or S100A9 protein.

The inhibitor as defined herein can be for use in the prevention or treatment of a myeloproliferative neoplasm, preferably a myeloproliferative neoplasm as defined herein above. In one embodiment, the inhibitor of the S100-protein, preferably at least one of S100A8 and S100A9, is an agent that prevents or reduces expression of the S100 protein in the cell, e.g. by interfering with transcription and/or translation of the S100 protein, such as e.g. S100 protein inhibitory nucleic acids or gene therapy vectors that knock out S100 protein expression. Preferably, the inhibitor is a small non-coding RNA.

Non-limiting examples of nucleic acids inhibiting S100 protein expression include miRNAs and siRNAs. However, the skilled person straightforwardly understands that other types of non-coding nucleic acid molecules can be equally suitable for inhibiting S100 protein expression, e.g. by interfering with splicing.

The inhibitor of the S100 protein, preferably of at least one of S100A8 and S100A9, can be one or more miRNAs. A miRNA inhibiting S100 protein expression preferably comprises a sequence that is complementary to a sequence present in the endogenous gene encoding said S100 protein. Preferably, a mature miRNA inhibiting the S100 protein comprises a seed region at the 5' end of the miRNA that is complementary to a sequence in the S100 protein gene. Preferably, the seed region comprises at least nucleotides 2-7 of the miRNA. The seed region can comprise nucleotides 2-8 of the mature miRNA. The miRNA can comprise additional nucleotides that are complementary to the S100 protein transcript, for example for 3'-supplementary pairing. Supplementary pairing is preferred in case the seed region is not 100% complementary to a sequence in the S100 protein transcript. Hence, the seed region can be at least about 80%, 85%, 90%, 95%, 96%, 97%, 98%, 99% or 100% complementary to a contiguous sequence in the S100 protein transcript. Preferably the sequence of at least the seed region of the miRNA is at least partly complementary to a sequence present in the untranslated region (UTR) of the S100 protein gene, preferably is at least partly complementary to a sequence present in the 3'-UTR. The interaction between the miRNA and the S100 protein transcript preferably causes inhibition of translation or degradation of the S100 protein transcript.

The inhibitor of the S100 protein, preferably of at least one of S100A8 and S100A9, can be one or more siRNAs. In one embodiment, the siRNA is designed such that it inhibits translation of a S100 protein transcript, preferably by RISC-mediated cleavage of the transcript. The skilled person understands how to design and construct siRNAs targeting the S100 protein transcript. Preferably, the siRNAs are designed such that they target a sequence that is specific to the S100 protein transcript. The length of the siRNA is preferably about 18-25 nt. Preferably, one strand of the siRNA is at least about 75%, 80%, 85%, 90%, 95%, 96%, 97%, 98%, or about 100% complementary to a contiguous sequence of the S100 protein transcript. Preferably, one strand of the siRNA (i.e. the guide strand) is fully complementary to a contiguous sequence in the S100 protein transcript. The contiguous sequence in the S100 protein transcript can be present in the 3'-UTR, 5'-UTR or coding sequence.

The inhibitor of the S100 protein, preferably of at least one of S100A8 and S100A9, can be one or more shRNAs. The skilled person understands how to design and construct an shRNA targeting and inhibiting the S100 protein transcript. Preferably, the shRNAs are designed such that they target a sequence that is specific to the S100 protein transcript. The shRNA can be embedded in e.g. a miRNA scaffold and/or are expressed e.g. as a primary transcript comprising the shRNA. Processing of the shRNA transcript results in a functional siRNA, which is incorporated into the RISC complex. This complex can subsequently inhibit the translation of the S100 protein transcript, preferably by cleaving the S100 protein mRNA transcript. Preferably, the shRNA comprises a contiguous sequence that has at least about 75%, 80%, 15 85%, 90%, 95%, 96%, 97%, 98%, or about 100% complementary to a contiguous sequence of the S100 protein transcript. Preferably, this contiguous sequence in the shRNA results in the guide strand of the siRNA after, preferably endogenous, processing of the shRNA. Preferably, the nucleotide sequence in the shRNA that is processed into the guide strand of the siRNA is fully complementary to a contiguous sequence in the T S100 protein transcript. The contiguous sequence in the S100 protein transcript can be present in the 3'-UTR, 5'-UTR or coding sequence.

Preferably, the agent inhibits specifically the expression of at least one of S100A8 and S100A9. Preferably, the agent inhibits specifically the expression of at least one of S100A8 and S100A9 and not any of the other S100 proteins.

The inhibitory nucleic acid as defined herein can be chemically modified, e.g. to enhance the efficacy and/or stability. The chemical modification can be at least one of a modification of the sugar moiety, a base modification and a phosphate modification. Chemical modifications on the sugar moiety include, but is not limited to, locked nucleic acids (LNA), unlocked nucleic acids (UNA), 2'-deoxy, 2'-O-methyl, 2'-fluoro, 2'-methoxyethyl and 2'-aminoethyl. Examples of base modifications include, but are not limited to hypoxanthine, 2,4-difluorotoluene, dihydrouridine, 2'-thiouridine and pseudouridine. Examples of phosphate modifications include, but is not limited to phosphorothioate, boranophosphate and peptide nucleic acids (PNA) (see for modifications e.g. the database siRNAmod, Dar et al, Sci Rep. (2016); 6:20031, incorporated herein by reference).

The inhibitor for use in the invention can be a combination of inhibitors, e.g. a pool of shRNAs, siRNAs and/or miRNAs. As a non-limiting example, the inhibitor can comprise at least 2, 3, 4, 5, 6, 7, 5 8, 9 or 10 different siRNAs and/or the inhibitor can comprise at least 2, 3, 4, 5, 6, 7, 8, 9 or 10 different miRNAs, or the inhibitor can comprise at least 2, 3, 4, 5, 6, 7, 8, 9 or 10 different shRNAs.

Alternatively or in addition, the inhibitor can comprise a combination of miRNAs and siRNAs, or miRNAs and shRNAs, or siRNAs and shRNAs, or a combination of siRNAs, shRNAs and miRNAs.

The inhibitory nucleic acid can be introduced into the cell, preferably a mesenchymal stromal cell, preferably a mesenchymal stromal cell located in the bone marrow, using any conventional method known in the art. The inhibitory nucleic acid can be directly introduced into the cell or is expressed from an expression vector. An expression vector for use in the invention can comprise an RNA polymerase II or III promoter to control the expression of a short hairpin RNA that is subsequently processed into an siRNA or an miRNA, preferably an miRNA or an siRNA as defined herein. A preferred expression vector is a naked DNA or a viral vector. A preferred naked DNA is a plasmid suitable for expression of the inhibitory nucleic acid as defined herein. A plasmid refers to a circular double stranded DNA into which additional DNA segments can be inserted, such as by standard molecular cloning techniques.

In one embodiment the expression vector is a viral vector. A preferred viral vector is a recombinant virus or virion. There are a wide variety of viral vectors known in the art that are suitable for introducing gene expression in a cell. The skilled person thus understands that the invention is not limited to any specific type of viral vector for introducing into a cell expression of the inhibitory nucleic acid molecule as defined herein. The viral vectors for use in the present invention can be any viral vectors suitable for infecting a human or animal. The vectors may be modified in any way known in the art, e.g. by deleting, inserting, mutating or modifying any viral areas. The viral vector can be selected from the group consisting of a retrovirus, a lentivirus, an adenovirus, an adeno-associated virus (AAV), a herpes simplex virus and a vaccinia virus. The viral vector can be a hybrid between two, or more, vectors.

The siRNA, shRNA, miRNA, plasmid expressing the shRNA, plasmid expressing the siRNA, or plasmid expressing the miRNA (or miRNA precursor), can be coupled to a carrier suitable for delivery into the cell. A preferred carrier is selected from the group consisting of a lipoplex, a liposome, a polymersome, a polyplex, a dendrimer, an inorganic nanoparticle, a virosome and cell penetrating peptides.

In one embodiment, the inhibitor of an S100 protein is an agent that prevents or reduces expression of the S100 protein in the cell, preferably mesenchymal stromal cell, preferably a mesenchymal stromal cell located in the bone marrow, by interfering with the transcription of the S100 protein transcript. Transcription can be inhibited by targeting (e.g. inhibiting or activating) an endogenous protein controlling the expression of an S100 protein.

In one embodiment, the inhibitor that prevents or reduces expression of the S100 protein, is selective for mesenchymal stromal cell, preferably a mesenchymal stromal cell located in the bone marrow, for example by specific expression or specific targeting of a vector or carrier. In addition or alternatively, specific expression can be achieved for example by the use of tumor- or tissue-specific promoters. Specific targeting can be achieved for example by coupling the vector or carrier to a (mesenchymal stromal cell) specific ligand.

The skilled person may use any conventional means to determine whether the inhibitor prevents or reduces the expression of an S100 protein as defined herein, preferably an S100A8 or S100A9 protein. Such conventional means may include, but are not limited to, transcriptome sequencing, Q-PCR and/or detecting, and optionally quantifying, S100 protein amounts.

The inhibitor may reduce at least about 10%, 20%, 30%, 40%, 50%, 60%, 70%, 80%, 90% or 100% of the expression of an S100 protein, preferably of an S100A8 or S100A9 protein, wherein 100% indicates a complete absence of the protein expression, as compared to the expression in a control cell. The control cell is preferably an identical cell, or cell type, but is not exposed to the inhibitor.

In one embodiment, the inhibitor of the S100-protein, preferably at least one of S100A8 and S100A9, is an agent that inhibits S100 protein functional activity. The agent that inhibits S100 protein functional activity can be a compound that is one or more of a small molecule, a peptide, a proteinaceous molecule, an aptamer, and an antibody. Preferably, the inhibitor is a small molecule.

The skilled person may use any conventional means to determine whether the agent inhibits S100 protein functional activity as defined herein, preferably inhibits S100A8 or S100A9 protein functional activity. Such conventional means may include, but are not limited to, ELISA assays, e.g. to measure secretion or reduced inflammation, and western blotting (see e.g. Vogl T et al, J Clin Invest. 2018; 128(5):1852-1866).

The inhibitor may inhibit at least about 10%, 20%, 30%, 40%, 50%, 60%, 70%, 80%, 90% or 100% of the functional activity of an S100 protein, preferably of an S100A8 or S100A9 protein, wherein 100% indicates a complete absence of functional activity as compared to a control. The control is preferably the activity of the S100 protein, preferably the S100A8 or S100A9 protein, that is not exposed to the inhibitor.

The inhibitor can be an antibody, or functional fragment thereof. Preferably the antibody or functional fragment thereof binds, preferably specifically binds an S100 protein as defined herein. Preferably the antibody or functional fragment thereof binds, preferably specifically binds, at least one of S100A8 and S100A9. Preferably, the antibody or functional fragment thereof binds, preferably specifically binds, at least one of S100A8 and S100A9 and inhibits its functional activity. Preferably the antibody is an S100 protein neutralizing antibody, preferably an S100A8 and/or S100A9 neutralizing antibody. The skilled person understands that the invention is not limited to any specific antibody or fragment thereof that can bind, preferably specifically bind, at least one of S100A8 and S100A9. Examples of such antibodies include, but is not limited to, the antibodies described in Hiratsuka et al, (Nat Cell Biol. 2006; 8(12):1369-75) and Vogl T et al, supra), which are incorporated herein by reference. Preferably, the antibody is a human or humanized antibody, such as, but not limited to, the humanized anti-S100A9 antibody described in WO2017008153A1.

The inhibitor is preferably a small molecule. The inhibitor is preferably a quinoline carboxamide. Processes for preparing therapeutically active quinoline carboxamides have been described in WO 03/106424 and WO 2012/004338, which are incorporated herein by reference. A deuterated form of a quinoline carboxamide is described in WO 2012/175541, which is incorporated herein by reference. Pharmaceutical compositions containing a salt of a quinoline carboxamide having enhanced stability during long-term storage at room temperature, methods for the manufacture of such compositions, crystalline salts of quinoline carboxamides and methods for preparing crystalline salts of quinoline carboxamides are described in WO 2005/074899, which is incorporated herein by reference.

A preferred inhibitor is a small molecule of formula (I)

(I)

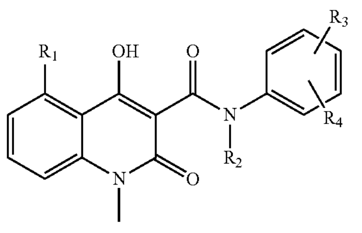

or a pharmaceutically acceptable salt thereof, wherein $R_1$ preferably is selected from the group consisting of H, methyl, ethyl, n-propyl, iso-propyl, methoxy, ethoxy, fluoro, chloro, bromo, trifluoromethyl, and trifluoromethoxy. In some embodiments, $R_1$ is selected from methyl, ethyl, n-propyl, iso-propyl, methoxy, ethoxy, fluoro, chloro, bromo, trifluoromethyl, and trifluoromethoxy. In some other embodiments, $R_1$ is selected from ethyl, n-propyl, iso-propyl, methoxy, ethoxy, chloro, bromo, trifluoromethyl, and trifluoromethoxy. In still other embodiments, $R_1$ is selected from ethyl, methoxy, chloro, and trifluoromethyl. In some particular embodiments, $R_1$ is methoxy.

The moiety $R_2$ preferably is a C1-C4 alkyl radical, which radical may be branched or linear. In some embodiments, $R_2$ is a C1-C3 alkyl radical. In some embodiments, $R_2$ is methyl or ethyl. In some particular embodiments, $R_2$ is methyl.

The moiety $R_3$ preferably is selected from methyl, methoxy, hydrogen, fluoro, chloro, bromo, trifluoromethyl, and trifluoromethoxy. In some embodiments, $R_3$ is selected from methyl, methoxy, fluoro, chloro, trifluoromethyl, and trifluoromethoxy. In some embodiments, $R_3$ is hydrogen or trifluoromethyl. In some embodiments, $R_3$ is trifluoromethyl.

$R_4$ is preferably selected from hydrogen, fluoro and chloro, with the proviso that $R_4$ is selected from fluoro and chloro only when $R_3$ is selected from fluoro and chloro. In some embodiments, $R_4$ is hydrogen or fluoro. In some particular embodiments, $R_4$ is hydrogen.

In some particular embodiments, in a compound of formula (I), $R_1$ and $R_4$ are as defined herein above;

$R_2$ is methyl or ethyl, in particular methyl; and $R_3$ is selected from methyl, methoxy, fluoro, chloro, trifluoromethyl, and trifluoromethoxy.

In some other particular embodiments, in a compound of formula (I), $R_1$ is as defined herein above;

$R_2$ is methyl or ethyl, in particular methyl;

$R_3$ is selected from methyl, methoxy, hydrogen, fluoro, chloro, trifluoromethyl, and trifluoromethoxy; and $R_4$ is H.

In some embodiments, $R_3$ is in para-position, i.e. the compound for use as defined herein may be represented by formula (Ia)

(Ia)

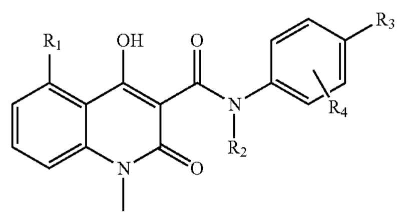

wherein $R_1$, $R_2$, $R_3$ and $R_4$ preferably are as defined herein above.

For example, in some embodiments of a compound of formula (Ia), $R_1$ and $R_4$ are preferably as defined herein above;

$R_2$ preferably is methyl or ethyl, in particular methyl; and $R_3$ preferably is selected from methyl, methoxy, hydrogen, fluoro, chloro, trifluoromethyl, and trifluoromethoxy.

In some other particular embodiments, in a compound of formula (Ia), $R_1$ preferably is as defined herein above;

$R_2$ preferably is methyl or ethyl, in particular methyl;

$R_3$ preferably is selected from methyl, methoxy, hydrogen, fluoro, chloro, trifluoromethyl, and trifluoromethoxy; and $R_4$ preferably is H.

As noted herein above, in some embodiments, $R_4$ is hydrogen. In those embodiments, the compound of formula (I) may be represented by formula (Ib)

(Ib)

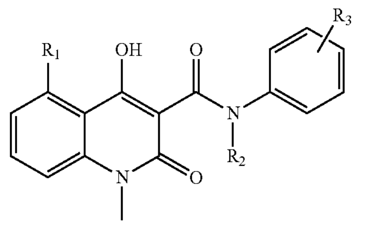

wherein $R_1$, $R_2$ and $R_3$ preferably are as defined herein above.

For example, in some embodiments of a compound of formula (Ib), $R_2$ is preferably methyl or ethyl, in particular methyl;

$R_3$ is preferably selected from methyl, methoxy, hydrogen, fluoro, chloro, trifluoromethyl, and trifluoromethoxy; and $R_1$ is preferably as defined herein above.

In some particular embodiments of a compound of formula (I), $R_3$ is in para-position and $R_4$ is H, and the compound for use as defined herein may then be represented by formula (Ic)

(Ic)

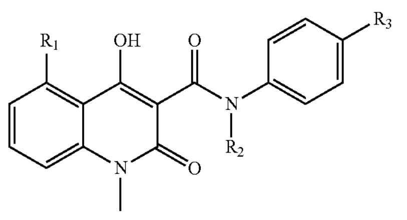

wherein $R_1$, $R_2$ and $R_3$ are as defined herein above.

In some particular embodiments of a compound of formula (Ic), $R_2$ preferably is methyl or ethyl, in particular methyl;

$R_3$ preferably is selected from methyl, methoxy, hydrogen, fluoro, chloro, trifluoromethyl, and trifluoromethoxy; and $R_1$ preferably is as defined herein.

For the purpose of the present invention, any reference to a compound of formula (I) also should be understood as a reference to a compound of any one of the formulas (Ia), (Ib) and (Ic), unless otherwise specified or apparent from the context.

In one embodiment, the compound of formula (I) is 4-hydroxy-5-methoxy-N,1-dimethyl-2-oxo-N-[4-(trifluoromethyl)phenyl]-1,2-dihydroquinoline-3-carboxamide (tasquinimod), of the structural formula:

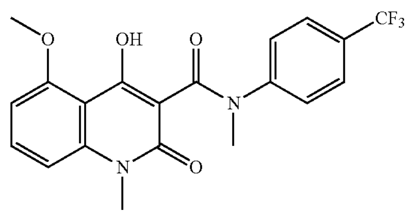 [SMILES: COc1cccc2c1c(O)c(C(=O)N(C)c1ccc(C(F)(F)F)cc1)c(=O)n2C]

A preferred inhibitor is tasquinimod or a functional equivalent thereof. A preferred inhibitor is tasquinimod or analogues thereof, for instance a small molecule of formula (I) as defined herein. Preferably, the inhibitor is tasquinimod. Tasquinimod (ABR-215050) is a known inhibitor of S100A9 (see e.g. JT Isaacs et al, "*Identification of ABR-*215050 *as lead second generation quinoline*-3-*carboxamide anti-angiogenic agent for the treatment of prostate cancer*". The Prostate. 66 (16): 1768-78). Compounds of formula (I), pharmaceutically acceptable salts thereof, deuterated forms thereof, crystalline salts thereof, and pharmaceutical compositions containing the compounds and their salts, as well as methods for preparing such compounds, their salts, deuterated forms and pharmaceutical compositions containing the compounds and their salts have been described in WO 99/55678, WO 00/03991, WO 03/106424, WO 2005/074899, WO 2012/004338, WO 2012/175541, WO 2016/042112 and WO 2016/078921, which documents are hereby incorporated by reference in their entireties into the present application.

In some embodiments, any reference to a compound of formula (I) also encompasses the deuterated form of thereof. As mentioned herein above, a deuterated form of tasquinimod is described in WO 2012/175541. The person of ordinary skill in the art will be capable of preparing analogously deuterated compounds of formula (I) by following the description of in said WO pamphlet. In some embodiments, thus, the compound of formula (I) has a deuterium enrichment in the moiety $R_2$ of formula (I) of at least 70%, more preferably at least 90%. For example, in some embodiments, $R_2$ is methyl having a deuterium enrichment of at least 70%, more preferably at least 90%. In some particular embodiments, the compound of formula (I) is tasquinimod having a deuterium enrichment in the amide-N methyl group of at least 70%, more preferably at least 90%. In some other embodiments, the compound of formula (I) is non-deuterated, having a deuterium content corresponding to the natural abundance of deuterium.

In an embodiment, the compound is the quinolone-3-carboxamide paquinimod (ABR-25757), having the structural formula:

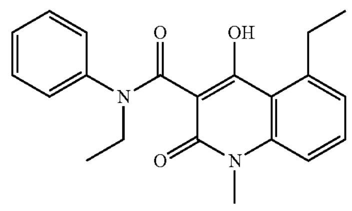 [SMILES: CCc1cccc2c1c(O)c(C(=O)N(CC)c1ccccc1)c(=O)n2C]

Paquinimod is a known inhibitor of S100A9 (see e.g. Schelbergen R F, et al. Ann Rheum Dis. 2015; 74(12):2254-8.). Hence in some embodiments, the inhibitor for use according to the invention has structural formula I), wherein $R_1$ and $R_2$ are ethyl and wherein $R_3$ and $R_4$ are hydrogen.

In one embodiment, the small molecule S100-protein inhibitor is a BET bromodomain inhibitor. A preferred BET bromodomain inhibitor is a thienotriazolodiazepine, preferably the known thienotriazolodiazepine JQ1. JQ1 is known in the art to suppress S100A8 and S100A9 mRNA and protein levels (Stewart et al, Bone Marrow Res. 2018, 31; 2018:5742954).

The inhibitor of an S100 protein for use according to the invention, preferably an S100A8 and/or S100A9 protein, is preferably not limited to an inhibitor that directly interferes with the S100 protein functional activity and/or expression. In addition or alternatively, the inhibitor may block or activate an upstream or downstream cellular component (e.g. protein or RNA) that subsequently results in inhibition of the expression and/or inhibition of the functional activity of the S100 protein, preferably of the S100A8 and/or S100A9 protein.

As a non-limiting example, the inhibitor may block downstream signalling of the TLR4 receptor, which subsequently results in the inhibition of S100A8/S100A9 expression and/or S100A8/S100A9 functional activity. Known small molecules that block the TLR4 receptor includes, but is not limited to, CLI-095 (TAK-242), as disclosed in e.g. Li M. et al., 2006. Mol. Pharmacol., 69:1288-1295 and Kawamoto T. et al., 2008, Eur J Pharmacol. 584(1):40-8.

As a further non-limiting example, the inhibitor may block the interaction between RAC1/RAC2, which subsequently results in the inhibition of S100A8/S100A9 expression and/or S100A8/S100A9 functional activity. Known small molecules that block RAC1/RAC2 interaction includes, but is not limited to, CAS No. 1177865-17-6 (chemical formula: $N^6$-[2-[[4-(Diethylamino)-1-methylbutyl]amino]-6-methyl-4-pyrimidinyl]-2-methyl-4,6-quinolinediamine trihydrochloride).

Dosage

In an embodiment, the inhibitor of an S100 protein, preferably an inhibitor as defined herein above is for the prevention or treatment of an MPN, preferably an MPN as defined herein above, wherein the inhibitor is administered at a total daily dose of about 0.05-10 mg.

It is understood that the terms "daily dose" and "total daily dose" are used interchangeably herein. In particular, the total daily dose can be administrated over one or several units (doses) per day as detailed herein below.

Preferably, the total daily dose is therapeutically effective and preferably also well tolerated, e.g. does not cause a side effect. A side effect is herein defined as an effect, whether therapeutic or adverse, that is secondary to the one intended. The side effect is preferably an adverse effect. Side effects can be graded as mild (grade 1), moderate (grade 2), severe (grade 3) or potentially life threatening (grade 4). Preferably, the administered total daily dose is well-tolerated, e.g. does not cause any side effects that are grade 1, 2, 3 and/or 4, preferably the administered total daily dose does not cause any side effects that are grade 1, 2 and/or grade 3 and more preferably the administered total daily dose does not cause any side effects that are grade 2 or 3.

Preferably, the administered total daily dose does not cause a very common, common, uncommon, rare or very rare side effect. More preferably the administered dose does not cause a very common, common, uncommon or rare side effect, even more preferably the administered total daily dose does not cause a very common, common or uncommon side effect and even more preferably the administered total daily dose does not cause a very common or common side effect. Most preferably the administered total daily dose does not cause a very common side effect.

A very common side effect is herein defined as the probability (chance) of experiencing the side effect is >=1/10, a common (frequent) side effect is herein defined as the probability of experiencing the side effect is >=1/100 and <1/10, an uncommon (infrequent) side effect is herein defined as the probability of experiencing the side effect is >=1/1000 and <1/100, a rare side effect is herein defined as the probability of experiencing the side effect is >=1/10000 and <1/1000 and a very rare side effect is herein defined as the probability of experiencing the side effect is <1/10000.

The inhibitor can be administered at the recommended maximum clinical dosage or at lower doses. Dosage levels of the inhibitor as defined herein may be varied so as to obtain a desired therapeutic response depending on the route of administration, severity of the disease and the response of the patient. When administered in combination with any further active agents, the active agents can be formulated as separate compositions that are given at the same time or different times, or the active agents can be given as a single composition.

The total daily dose of the S100 protein inhibitor is preferably in the range of 0.05-10 mg. Preferably, the total daily dose of a small molecule S100 protein inhibitor as defined herein is in the range of 0.05-10 mg. Preferably, the total daily dose of tasquinimod is in the range of 0.05-10 mg.

Preferably the total daily dose is in the range of about 0.05-10 mg, 0.06-9 mg, 0.07-8 mg, 0.08-7 mg, 0.09-6 mg, 0.1-5 mg, 0.2-4 mg, 0.3-3 mg, 0.4-2 mg, 0.5-1 mg or 0.25-1 mg. Preferably, the total daily dose is about 0.10 mg, 0.15 mg, 0.20 mg, 0.25 mg, 0.30 mg, 0.40 mg, 0.50 mg, 0.60 mg, 0.70 mg, 0.80 mg, 0.90 mg, 1.0 mg, 1.2 mg, 1.4 mg, 1.6 mg, 1.8 mg, 2.0 mg, 2.5 mg, 3.0 mg, 3.5 mg, 4.0 mg, 4.5 mg or about 5.0 mg. Preferably, the total daily dose is about 0.52 mg, 0.5 mg or 1 mg. Preferably, the total daily dose is about 1 mg.

The total daily dose can be divided over several doses per day. These separate doses may differ in amount. For example for each total daily dose, the first dose may have a larger amount of the compound than the second dose or vice versa. However preferably, the compound is administered in similar or equal doses. The inhibitor may be administered 1, 2, 3, 4, 5 times per day, or more often. Preferably, the inhibitor is administered once a day. The inhibitor may also be administered once every 2, 3, 4, 5, 6, 7, 8, 9, 10 or more days.

Modes of Administration

The inhibitor, or a composition comprising the inhibitor, as defined herein may be administered enterally, orally, parenterally, sublingually, by inhalation (e. g. as mists or sprays), rectally, or topically, preferably in dosage unit formulations containing conventional nontoxic pharmaceutically or physiologically acceptable carriers, adjuvants, and vehicles as desired. Preferably the inhibitor, or a composition comprising the inhibitor, is administered orally.

For example, suitable modes of administration include oral, subcutaneous, transdermal, transmucosal, iontophoretic, intravenous, intraarterial, intramuscular, intraperitoneal, intranasal (e. g. via nasal mucosa), subdural, rectal, gastrointestinal, and the like, and directly to a specific or affected organ or tissue, e.g. a cancerous tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques.

The inhibitor of an S100 protein as defined herein can be mixed with pharmaceutically acceptable carriers, adjuvants, and vehicles appropriate for the desired route of administration. The inhibitor as defined herein may be administered by supplementation via gastric or percutaneous tubes.

In a preferred embodiment the invention pertains to an inhibitor as defined herein above, for use in treating, preventing, or suppressing symptoms associated with a MPN by administration of an effective total daily dose for a specified period of time.

The dosage form for oral administration can be a solid oral dosage form. The class of solid oral dosage forms consists primarily of tablets and capsules, although other forms are known in the art and can be equally suitable. When used as a solid oral dosage form, an inhibitor or a composition comprising an inhibitor as defined herein, may e.g. be administered in the form of an immediate release tablet (or a capsule and the like) or a sustained release tablet (or a capsule and the like). Any suitable immediate release or sustained release solid dosage forms can be used in the context of the invention as will be evident for the skilled person.

A composition as described herein, for a use as described herein, can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The composition can also be administered in liposome formulations. The composition comprising the S100 protein inhibitor can be administered as prodrugs, where the prodrug undergoes transformation in the treated subject to a form which is therapeutically effective. Additional methods of administration are known in the art.

Preferably a composition comprising a compound as defined herein, preferably a sulphonamide as defined herein, is administered orally or parenterally.

Compositions

In an aspect, the invention pertains to a composition comprising an inhibitor of an S100 protein as defined herein. The composition may be suitable for use in cell culture, preferably animal cell culture, more preferably mammalian cell culture. The composition preferably is a pharmaceutical composition. The composition is preferably for a use in the prevention or treatment of a myeloproliferative neoplasm (MPN), preferably an MPN as defined herein above.

A composition may comprise one type of compound as defined herein or a combination of compounds as defined herein, e.g. a combination of S100 protein inhibitors. A composition may comprise at least 1, 2, 3 or more different types of S100 protein inhibitors.

The composition may comprise an S100 protein inhibitor together with a physiologically acceptable carrier. In particular, the composition can be formulated as pharmaceutical composition by formulation with additives such as pharmaceutically or physiologically acceptable excipients, carriers, and vehicles.

Suitable pharmaceutically or physiologically acceptable excipients, carriers and vehicles can include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-P-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003), $21^{st}$ edition (2005) and $22^{nd}$ edition (2012), incorporated herein by reference.

Pharmaceutical compositions as described herein for use according to the invention may be in any form suitable for the intended method of administration, including, for example, a solution, a suspension, or an emulsion. In a preferred embodiment, a composition as defined herein is administered in a solid form or in a liquid form.

Solid dosage forms for oral administration may include capsules, tablets, pills, powders, and granules. In such solid dosage forms the composition, preferably a composition comprising a S100 protein inhibitor as described herein, may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings. Preferably, the composition is in the form of a capsule.

Liquid dosage forms for oral administration may include pharmaceutically acceptable emulsions, solutions, suspensions, syrups, and elixirs containing inert diluents commonly used in the art, such as water or saline. Such compositions may also comprise adjuvants, such as wetting agents, emulsifying and suspending agents, cyclodextrins, and sweetening, flavoring, and perfuming agents.

Liquid carriers are typically used in preparing solutions, suspensions, and emulsions. Liquid carriers/liquid dosage forms contemplated for use in the practice of the present invention include, for example, water, saline, pharmaceutically acceptable organic solvent(s), pharmaceutically acceptable oils or fats, and the like, as well as mixtures of two or more thereof.

A composition as described herein can be admixed with an aqueous solution prior to administration. The aqueous solution should be suitable for administration and such aqueous solutions are well known in the art. It is further known in the art that the suitability of an aqueous solution for administration may be dependent on the route of administration. The aqueous solution is an isotonic aqueous solution. The isotonic aqueous solution preferably is almost (or completely) isotonic to blood plasma. In an even more preferred embodiment, the isotonic aqueous solution is saline.

The liquid carrier may contain other suitable pharmaceutically acceptable additives such as solubilizers, emulsifiers, nutrients, buffers, preservatives, suspending agents, thickening agents, viscosity regulators, stabilizers, flavorants and the like. Preferred flavorants are sweeteners, such as monosaccharides and/or disaccharides. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the composition as defined herein can be prepared by mixing with a suitable nonirritating excipient such as cocoa butter and polyethylene glycols that are solid at room temperature but liquid at the rectal temperature and will therefore melt in the rectum and release the compound and/or immune checkpoint blocking agent.

For parenteral administration, the carrier can also be an oily ester such as ethyl oleate, isopropyl myristate, and the like. Compositions for use in the present invention may also be in the form of microparticles, microcapsules, liposomal encapsulates, and the like, as well as combinations of any two or more thereof.

Time-release, sustained release or controlled release delivery systems may be used for administration of one or more of the compositions as described herein, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly (phosphazenes).

A composition as defined herein can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound, immune checkpoint blocking agent or a combination of a compound and an immune checkpoint blocking agent as defined herein, stabilizers, preservatives, excipients, and the like. The preferred lipids are the phospholipids and phosphatidyl cholines (lecithins), both natural and synthetic. Methods to form liposomes are known in the art. See, for example, Prescott, Ed., Methods in Cell Biology, Volume XIV, Academic Press, New York, N. Y., p. 33 et seq (1976).

A pharmaceutical composition as defined herein, i.e. comprising an S100 protein inhibitor, can comprise a unit dose formulation, wherein the unit dose is a dose sufficient to have a therapeutic or preventive effect of a myeloproliferative neoplasm as defined herein, and/or an amount effective to reduce, or knock out, the expression of a S100 protein in a cell, preferably a mesenchymal stromal cell, preferably a mesenchymal stromal cell located in the bone marrow The unit dose may be sufficient as a single dose to have a preventive and/or therapeutic effect of a MPN, preferably of a MPN as defined herein. Alternatively, the unit dose may be a dose administered periodically in a course of treatment of a MPN, preferably a MPN as defined herein. During the course of the treatment, the concentration of the subject compositions may be monitored to insure that the desired level is maintained.

While the compound for use as described herein can be administered as the sole active pharmaceutical agent, they can also be used in combination with one or more other agents known in the art to be used for the treatment or prevention of an MPN.

The current goal for the treatment of MPN is to reduce the number of increased blood cells and to help control any complications as bleeding or blood clotting.

Venesection (or phlebotomy) is a procedure in which a controlled amount of blood is removed from the bloodstream. For many people, particularly younger patients and those with mild disease, regular venesection (every few months) may be all that is needed to control their disease for many years. Chemotherapy is a further option, mostly myelosuppressive agents as hydroxyurea (oral capsule chemotherapy). Interferon is sometimes prescribed for younger patients to help control the production of blood cells. Interferon can be given as an injection under the skin (subcutaneous injection). Many people are prescribed daily doses of aspirin, which have been shown to reduce the risk of thrombosis. Anagrelide hydrochloride (Agrylin) is a drug used to reduce high platelet counts. Anagrelide can be taken in capsule form by mouth.

Myelofibrosis is typically associated with enlargement of the spleen (splenomegaly). Chemotherapy such as hydroxyurea, or thalidomide may be used to reduce an enlarged spleen. In some cases, the surgical removal of the spleen (splenectomy) may be considered. Small doses of radiation to the spleen can also be given to reduce its size. This usually provides temporary relief for about three to six months. Myelofibrosis is generally regarded as incurable. Some younger patients who have a suitably matched donor may be offered an allogeneic (donor) stem cell transplant. Stem cell transplants carry significant risks and are only suitable for a small minority of younger patients (usually under 60 years). A common other treatment in myelofibrosis are JAK2 inhibitors which work by blocking the activity of the JAK2 protein, which may lead to a reduction in splenomegaly and decreased symptoms. They also work in patients with myelofibrosis without the JAK2 mutation. A number of JAK2 inhibitors are in clinical trials. The problem is that some patients never respond to JAK2 inhibition or become resistant over time. Moreover JAK2 inhibitors are known to cause cytopenia (a reduction in the number of mature blood cells), rendering JAK2 inhibitors unsuitable for use in the treatment of patients having myelofibrosis in combination with cytopenia.

Prior to the present invention, there was no treatment available for a subject suffering from myelofibrosis in combination with cytopenia. The S100 protein inhibitors as described herein, in particular the S100A8/A9 protein inhibitors described herein, may thus be particularly useful for the treatment of a subject suffering from myelofibrosis in combination with cytopenia.

In addition or alternatively, an S100 protein inhibitor for use in the prevention or treatment of an MPN as defined herein can be used in combination with at least one of radiation therapy, chemotherapy, and stem cell transplantation. The stem cell transplantation is preferably a bone marrow stem cell transplantation.

An S100 protein inhibitor for use in the prevention or treatment of an MPN as defined herein can be used in combination with a myelosuppressive agent. An S100 protein inhibitor for use in the prevention or treatment of an MPN as defined herein can be used in combination with an agent selected from the group consisting of hydroxyurea, thalidomide, interferon, aspirin, anagrelide hydrochloride and an JAK2 inhibitor, or any combination thereof. The S100 protein inhibitor for use in the prevention or treatment of an MPN as defined herein can be used in combination with a JAK2 inhibitor. A preferred JAK2 inhibitor may be ruxolitinib or fedratinib. The inventors discovered that a combined inhibition of the inflammatory axis through S100A8/S100A9 in combination with Ruxolitinib will lead to more efficient inhibition of MPN-associated inflammation (data not shown).

In addition or alternatively, the S100 protein inhibitor for use in the prevention or treatment of an MPN as defined herein can be used in combination with at least one of venesection, splenectomy and a stem cell transplantation.

Further representative agents useful in combination with the inhibitor, for the treatment of an MPN include, but are not limited to, Coenzyme Q, vitamin E, idebenone, MitoQ, EPI-743, vitamin K and analogues thereof, naphtoquinones and derivatives thereof, other vitamins, and antioxidant compounds.

When further active agents are used in combination with an inhibitor as defined herein, the further active agents may generally be employed in therapeutic amounts as indicated in the Physicians' Desk Reference (PDR) 53rd Edition (1999), which is incorporated herein by reference, or such therapeutically useful amounts as would be known to one of ordinary skill in the art.

A composition as described herein, can be prepared as a medicinal or cosmetic preparation or in various other media, such as foods for humans or animals, including medical foods and dietary supplements.

A "medical food" is a product that is intended for the specific dietary management of a disease or condition for which distinctive nutritional requirements exist. By way of example, but not limitation, medical foods may include vitamin and mineral formulations fed through a feeding tube (referred to as enteral administration).

A "dietary supplement" shall mean a product that is intended to supplement the human diet and is typically provided in the form of a pill, capsule, and tablet or like formulation. By way of example, but not limitation, a dietary supplement may include one or more of the following ingredients: vitamins, minerals, herbs, botanicals; amino acids, dietary substances intended to supplement the diet by increasing total dietary intake, and concentrates, metabolites, constituents, extracts or combinations of any of the foregoing. Dietary supplements may also be incorporated into food, including, but not limited to, food bars, beverages, powders, cereals, cooked foods, food additives and candies.

The subject composition thus may be compounded with other physiologically acceptable materials which can be ingested including, but not limited to, foods. In addition or alternatively, the compositions for use as described herein may be administered orally in combination with (the separate) administration of food.

Kit of Parts

One or more of the pharmaceutical compositions as defined herein may be comprised in a kit of parts. In an aspect, the invention relates to a kit of parts comprising one or more compositions, preferably pharmaceutical compositions, as defined herein above. Preferably, a kit of parts as defined herein is for a use in the treatment of an MPN, preferably an MPN as defined herein.

Optionally, the kit of parts further comprises a leaflet. The leaflet may comprise instructions for use. In addition or alternatively, the leaflet may be at least one of a patient information leaflet and a Summary of Product Characteristics (an SmPC). Preferably the instructions specify the use of the inhibitor of an S100 protein as defined herein, or the composition comprising the inhibitor, for the prevention or treatment of an MPN, preferably an MPN as defined herein.

Diagnostic Method

The MPN as defined herein may be characterized by myeloproliferation and subsequent myelofibrosis. At the onset of myelofibrosis patients are often too sick to commence any treatment. Hence it is of key relevance to determine at an early stage whether a subject is, or is going to, develop myelofibrosis. The presence, or increased presence, of an S100 protein, preferably of an S100A8/A9 protein in a biological sample can be indicative of a myeloproliferative neoplasm. Moreover, an increase in S100 proteins, preferably at least one of S100A8 and S100A9, is indicative of disease progression from a myeloproliferative to a myelofibrosis phase. Indeed the inventors discovered that S100A8/S100A9 levels increase with advancing disease and progressing fibrosis. S100, and in particular S100A8/A9, proteins can thus function as a reliably biomarker to predict the individual transition from the myeloproliferation phase to the life-threatening myelofibrosis phase.

In an aspect, the invention therefore pertains to a (diagnostic) method for identifying a subject suffering from a myeloproliferative neoplasm, comprising a step of detecting the presence of an S100 protein, preferably S100A8 or S100A9, in a biological sample.

The method may be an in vivo method. Preferably the method is an ex vivo method, preferably an in vitro method. In this embodiment, the S100 protein, preferably at least one of S100A8 and S100A9, functions as a diagnostic marker for a myeloproliferative neoplasm. Preferably, the S100 protein is a diagnostic marker for the severity of the myeloproliferative neoplasm, e.g. a fibrosis grade 0, 1, 2 or 3. MPN with fibrosis grade 0 is characterised by myeloproliferation, while MPN with fibrosis grades 1, 2 and 3 are characterized by an increased severity of myelofibrosis.

The term "diagnostic marker", "marker for diagnosing" and "marker for diagnosis", as used herein, is intended to indicate a biological parameter capable of (aiding in) the identification of a myeloproliferative neoplasm. More precisely the presence, or increased presence, of an S100 protein as defined herein, preferably at least one of S100A8/A9, is indicative of a myeloproliferative neoplasm (MPN), wherein preferably the MPN is selected from the group consisting of primary myelofibrosis, essential thrombocythemia, polycythemia vera, Chronic neutrophilic leukemia, chronic myelogenous leukemia, chronic eosinophilic leukemia and mastocytosis. Preferably, the presence, or increased presence, of an S100 protein as defined herein in a biological sample is indicative of a primary myelofibrosis, preferably of a primary myelofibrosis Grade 0, 1, 2, or 3.

The increase in an S100 protein as defined herein, preferably at least one of S100A8/A9, in a biological sample may indicate whether the disease progresses from a myeloproliferative phase (i.e. "Grade 0 myelofibrosis") to a myelofibrosis phase (i.e. Grade 1, 2, or 3 myelofibrosis). For example while in the myeloproliferative phase, the median survival of polycythemia vera (PV) and essential thrombocythemia (ET) is about 15 years, it dramatically drops to only about 1.5 years once the disease progresses to myelofibrosis (MF), which is comparable to the median survival of advanced solid tumors. Hence the S100, in particular the S100A8/A9, biomarker of the invention may assist to define risk groups of patients and to individually monitor the disease course overtime. In addition, the biomarker specifically allows to determine the "risk point" for disease acceleration which is crucial for clinical decision making. While fibrosis is only apparent quite late in routine diagnostics, the S100 biomarker predicts the fibrotic transformation (exemplified in FIG. 5).

The biological sample may be any biological sample suitable for the detection of an S100 protein as defined herein. The biological sample is preferably a bone marrow sample or a blood sample. The presence of the S100 protein as defined herein, preferably the presence of at least one of S100A8 and S100A9, is preferably detected in a serum or plasma sample. Alternatively or in addition, the presence of the S100 protein as defined herein, preferably at least one of S100A8 and S100A9, is detected in a bone morrow sample. Preferably, the S100 protein is detected in the mesenchymal stromal cells of the bone marrow. Preferably, the presence of the S100 protein as defined herein, preferably at least one of S100A8 and S100A9 is detected in one or more fibrosis-driven cells. Preferably, the presence of the S100 protein as defined herein, preferably at least one of S100A8 and S100A9 is detected in one or more MSC-1 cells. Preferably, the presence of the S100 protein as defined herein, preferably at least one of S100A8 and S100A9 is detected in one or more MSC-2 cells. Preferably, the presence of the S100 protein as defined herein, preferably at least one of S100A8 and S100A9 is detected in one or more Gli1+ MSC cells.

The detected level of the S100 protein in a biological sample can be compared to the level of the S100 protein in a control sample. The level of the S100 protein in a control sample may be known in the art and a control sample does not have to be included in the diagnostic method. Alternatively, the method also includes the detection of the S100 protein, preferably S100A8 or S100A9, in the control sample. A control sample is a preferably a biological sample, preferably a blood or bone marrow sample, of an individual not suffering from an MPN. An increase in the level of the S100 protein, preferably of S100A8 or S100A9, can be indicative of a MPN. A subject may be diagnosed with an MPN, preferably with an MPN as defined herein, if the level of the S100 protein is increased at least 1, 2, 3, 4, 5, 10-fold or more.

Alternatively or in addition the control sample is a biological sample, preferably a blood or bone marrow sample, taken from the same individual, wherein the sample is obtained at an earlier point in time. Hence the level of the S100 protein as defined herein, preferably at least one of S100A8 and S100A9, may be monitored over time and compared with a previously obtained biological sample of the same individual. The control sample may be a sample taken from the same individual, wherein the control sample was obtained at least 1, 2, 3, 4, 5 or 6 months earlier or, e.g. at least 1, 2, 3, 4 or 5 years earlier. The control sample may be a sample taken from the same individual, which control sample was obtained at most 1, 2, 3, 4 or 5 years earlier or, e.g. at most 1, 2, 3, 4, 5 or 6 months earlier, Using the (diagnostic) method of the invention, a subject can be diagnosed with an MPN even before the onset of the fibrotic phase, as the levels of the S100 protein, preferably the level of at least one of the S100A8 and S100A9 protein, may be increased in a biological sample even before bone marrow fibrosis is detectable (as exemplified in FIG. 5). In an embodiment, several biological samples can be taken overtime, e.g. to monitor the progression of the MPN. The level of the S100 protein, preferably of the S100A8 and/or S100A9 protein, can be monitored in a biological sample at least once every 1, 2, 3, 4, 5 or 6 months or less frequent. Alternatively or in addition, the level of the S100 protein, preferably of the S100A8 and/or S100A9 protein, can be monitored at least once every 1, 2, 3, 4 or 5 years or less frequent.

The inventors discovered that an increase in S100 protein levels, in particular S100A8 and/or S100A9 protein levels, is correlated with MPN progression. The increase in S100 protein levels, in particular S100A8/A9 protein levels, can therefore be used as a biomarker for MPN severity and for stratifying patients. The invention pertains to a diagnostic method for stratifying patients, comprising a step of detecting the presence of an S100 protein, preferably an S100 protein as defined herein, by exposing the biological sample to an agent as defined herein. The biomarker may serve as a patient stratification biomarker.

A subject may be stratified into having Grade 0, Grade 1, grade 2, or Grade 3 primary myelofibrosis. A subject may be diagnosed with primary myelofibrosis Grade 0, if the level of the S100 protein, preferably S100A8 and/or S100A9, is increased at least 1, 2, 3, 4, 5, 10-fold or more, preferably as compared to a control sample. A subject may be diagnosed with primary myelofibrosis Grade 1, if the level of the S100 protein, preferably S100A8 and/or S100A9, is increased at least 1, 2, 3, 4, 5, 10-fold or more, preferably as compared to a control sample. A subject may be diagnosed with primary myelofibrosis Grade 2, if the level of the S100 protein, preferably S100A8 and/or S100A9, is increased at least 1, 2, 3, 4, 5, 10-fold or more, preferably as compared to a control sample. A subject may be diagnosed with of primary myelofibrosis Grade 3, if the level of the S100 protein, preferably S100A8 and/or S100A9, is increased at least 1, 2, 3, 4, 5, 10-fold or more, preferably as compared to a control sample.

The subject may have a myeloproliferative neoplasm, which is characterized by an excess production of mature blood cells (myeloproliferation). The inventors discovered that an increase in S100 protein levels, preferably S100A8/A9, indicates that the myeloproliferative phase is progressing into the myelofibrotic phase. Hence in the method of the invention, a subject may be diagnosed with an increased risk for progression into a myelofibrotic phase, when the S100 protein levels increase, preferably increase at least 1, 2, 3, 4, 5, 10-fold or more, and preferably as compared to a control sample. Preferably, a subject suffering from an MPN having a myeloproliferative phase may be diagnosed with an increased risk for progression into the myelofibrotic phase, when the S100 protein levels increase, preferably increase at least 1, 2, 3, 4, 5, 10-fold or more, and preferably as compared to a control sample. The (diagnostic) method of the invention may comprise a step of detecting the presence of an S100 protein, preferably an S100 protein as defined herein, by exposing the biological sample to an agent as defined herein.

Alternatively or in addition, the diagnostic method may be a companion diagnostic method, e.g. to monitor treatment and/or to determine the efficacy of a treatment, preferably a treatment as defined herein. Preferably, the invention pertains to a method to identify a subject that will benefit from a treatment with an inhibitor of an S100 protein as defined herein, preferably the method will identify a subject that benefits from a treatment with an inhibitor of an S100A8 and/or S100A9 protein as defined herein. The method preferably comprises a step of detecting the presence of an S100 protein, preferably S100A8 and/or S100A9, in a biological sample, preferably a biological sample as defined herein.

The method is preferably an ex vivo method. Preferably, the subject is identified as benefitting from the treatment when the presence of the S100 protein, preferably S100A8 and/or S100A9, is increased as compared to a control sample. The control sample is preferably a control sample as defined herein. Preferably the subject benefitting from the treatment suffers from Grade 0, 1, 2 or 3 primary myelofibrosis.

In a preferred method of the invention, a subject may be stratified into responsive or non-responsive to an inhibitor of an S100 protein as defined herein. Preferably in a method of the invention, a subject may be stratified into responsive or not responsive to an inhibitor of an S100A8/A9 protein as defined herein.

In an aspect, the invention concerns an agent for identifying a subject suffering from, or at risk of, a myeloproliferative neoplasm, wherein the agent binds to an S100 protein, preferably an S100A8 or S100A9 protein. Preferably the agent specifically binds to at least one of the S100A8 and S100A9 proteins. More preferably the agent specifically binds to at least one of the S100A8 and S100A9 proteins and not to any of the other S100 proteins.

An agent binding a diagnostic marker as described herein can be selected from the group consisting of a small molecule, an antibody, a nucleic acid, a proteinaceous molecule, an aptamer, or an antigen-binding fragment thereof. Such agents may further comprise a detectable signal or label, such as a radioisotope, a fluorescent molecule or biotin.

The agent binding to an S100 protein, preferably an S100A8 or S100A9 protein as defined herein, can be an inhibitor of the S100 protein, preferably an inhibitor as defined herein above. The agent binding to an S100 protein, preferably an S100A8 or S100A9 protein as defined herein, can be an antibody, or functional fragment thereof, as defined herein above. Alternatively, the agent binding to an S100 protein, preferably an S100A8 or S100A9 protein as defined herein, can be an small molecule, preferably a small molecule as defined herein above. The agent binding to an S100 protein, preferably an S100A8 or S100A9 protein as defined herein, can be tasquinimod, preferably deuterium-enriched tasquinimod.

An antibody or antigen-binding fragment thereof for detecting a biomarker as described herein may selectively bind to a biomarker as described herein. Preferably an antibody or antigen-binding fragment thereof may bind to an S100 protein as described herein, wherein preferably the S100 protein is at least one of S100A8 or S100A9.

The step of detecting a diagnostic marker can be performed using any conventional method known in the art. As non-limiting examples, the diagnostic marker can be detected using an agent capable of binding a diagnostic marker as described herein.

Non-limiting examples for detecting the biomarker as defined herein include, but are not limited to, (quantitative) PCR, enzyme-linked immunosorbent assay (ELISA), gel electrophoresis, surface plasmon resonance (SPR), Mass-sensing BioCD protein array, surface enhanced Raman spectroscopy (SERS), colorimetric assay, electrochemical assay, and fluorescence methods.

The invention further pertains to a kit comprising an agent as defined herein and to the use of an agent as defined herein to identify a subject that suffers from an MPN, preferably an MPN as defined herein.

The present invention has been described above with reference to a number of exemplary embodiments as shown in the drawings. Modifications and alternative implementations of some parts or elements are possible, and are included in the scope of protection as defined in the appended claims.

FIGURE LEGENDS

FIG. 1: Mesenchymal stromal cells-1 and 2 are reprogrammed towards a pro-fibrotic profile in JAK2V617F induced primary myelofibrosis and up-regulate S100a8/S100a9. (A) Representative HE and reticulin staining (20× magnification) of bone marrows analyzed by single cell RNA sequencing in JAK2 (V617F) induced bone marrow fibrosis or control (JAK2 EV, n=4 mice per condition). (B) UMAP visualization of clustering of the non-hematopoietic bone marrow niche as identified by unsupervised clustering (n=1292 cells). Dashed lines highlight the four major cell populations. (C) Ridgeline plot comparing the expression of hallmark matrisome gene sets in MSC and OLC clusters comparing the experimental (JAK2 (V617F) and control (JAK2 (EV) condition. For aggregated gene expression the cumulative gene expression of each geneset per cell was normalized as described (Butler, A. et al. (2018), Nature biotechnology, 36 (5), pp. 411-420) (Butler et al., 2018). Significance was determined by competitive gene set enrichment analysis. (D) Normalized differential gene expression (ThPO vs. EV) of indicated genes in the four MSC populations organized by biological processes/terms (Wilcoxon rank sum test, two tailed).

FIG. 2: Mesenchymal stromal cells in patients with JAK2V617F induced primary myelofibrosis acquire a pro-fibrotic profile and up-regulate S100A8/S100A9. (A) Representative HE and reticulin staining (20× magnification) of bone marrows analyzed by single cell RNA sequencing in a patient with JAK2 (V617F) primary myelofibrosis (PMF) (MF grade 2) and 2 control patients (lymphoma without bone marrow contribution). (B) UMAP visualization of clustering of the non-hematopoietic bone marrow niche as identified by unsupervised clustering. Dashed lines highlight the four major cell populations. Comparison of populations in PMF and normal bone marrow show that all cell populations are present in both conditions. (C) Ridgeline plot comparing the expression of 1) hematopoiesis-support, 2) MSC signature, 3) the hallmark collagens in the PMF patient and in controls. For aggregated gene expression the cumulative gene expression of each geneset per cell was normalized as described (Butler et al, supra) (Butler et al., 2018). Significance was determined by competitive gene set enrichment analysis. (D) Normalized differential gene expression (ThPO vs. EV) of S100A8/S100A9 (Wilcoxon rank sum test, two tailed). (E) The receptor ligand interactions analyzed with Cellphone DB indicated increased interaction between S100A8/S100A9 and RAC1/RAC2 and RAC1 is indeed the top up-regulated receptor in both murine models and patient samples in PMF, indicating that this is also an interesting therapeutic target downstream of S00A8/S100A9.

FIG. 3: S100A8/S100A9 are a biomarker for MPN disease progression. (A) Quantification of S100A8 in the plasma (peripheral blood) by ELISA. Patients without hematological malignancy (n=96) were compared to patients with verified MPN (n=155; t-test, two-sided; A) and different stages of reticulin fibrosis (B; One-way-ANOVA, post-hoc pairwise t-test). The steep increase in S100A8 levels with onset of fibrosis (MF0 to MF1) indicates that S100A8 tracks the progression/onset of bone marrow fibrosis. (C) Representative immunohistochemical staining of S100A8+ cells (20× magnification) in control bone marrows (myelofibrosis/reticulin grade 0) and MPN patients with different grades of bone marrow fibrosis. (D) Quantification of S100A8 expression in the stroma of patients according to a newly established S100A8 grading score: 0=no expression in the stroma; 1=faint expression in spindle-shaped and bone-aligning cells; 2=expression in the interstitial space; 3=strong staining.

FIG. 4: Tasquinimod treatment in JAK2(V617F)-induced fibrosis normalizes splenomegaly and leukocytosis, and reduces fibrosis in bone marrow. (A) Mice transplanted with JAK2(V617F)- or JAK2(WT)-transduced ckit+ cells received tasquinimod (ABR-215050) treatment (30 mg/kg/day in drinking water) or vehicle from 5 weeks until 10 weeks, and from 13 until 20 weeks post-transplant. N=7-10/group. (B) White blood cell counts from peripheral blood measured overtime. (C) Overview images of spleens from mice transplanted with JAK2(V617F)- or JAK2(WT)-BM cells receiving tasquinimod or vehicle treatment. (D) Spleen weights normalized to mouse weight. (E) Platelets counts in peripheral blood measured over time. (F) Representative images of reticulin staining in mice transplanted with JAK2 (V617F)- or JAK2(WT)-BM cells receiving tasquinimod or vehicle treatment. 10×, scale bar: 250 μm. (G) Mean reticulin grade in mice transplanted with JAK2(V617F)- or JAK2(WT)-BM cells receiving tasquinimod or vehicle treatment. (H) Representative images of HE staining in control and treated mice. 20×, 100 μm.

Figure 5:
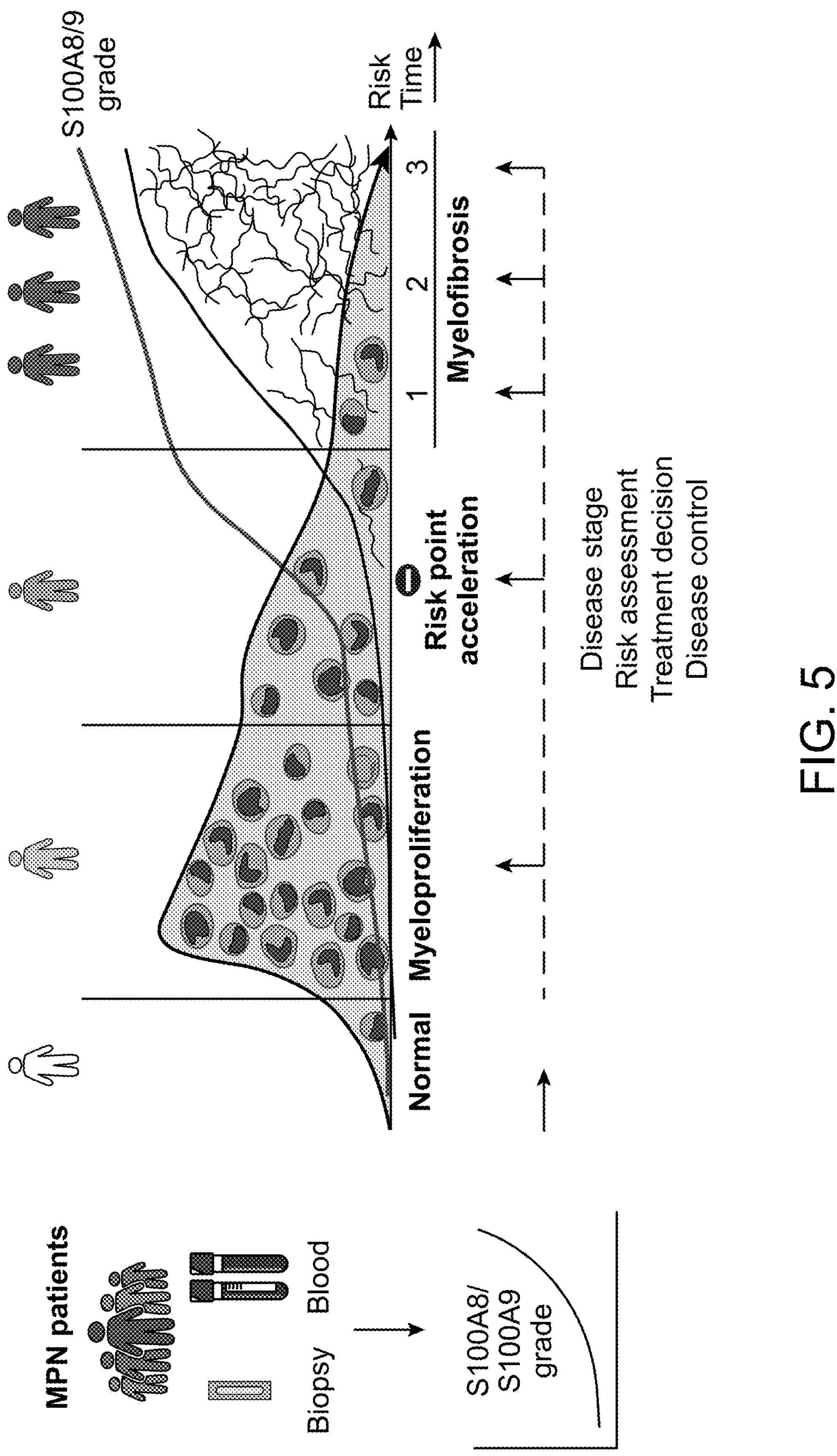

FIG. 5: Schematic representation for the use of S100A8/A9 as a targetable biomarker. Bone marrow biopsies and blood samples are routinely taken in the follow up of the heterogeneous group of MPN patients. The S100A8/S100A9 levels will be defined in blood and/or bone marrow over times/during treatment. The S100A8/S100A9 biomarker will not only assist to define risk groups of patients but also individually monitor the disease course over time. The biomarker specifically determines the "risk point" for disease acceleration which is crucial for clinical decision making. While fibrosis is only apparent quite late in routine diagnostics, the biomarker can determine the fibrotic transformation. Additionally, it will be crucial to monitor therapy response and will be a companion diagnostic for e.g. Tasquinimod treatment.

EXAMPLES

Materials and Methods

Viral Transduction

For retroviral and lentiviral transduction, c-kit$^+$-enriched cells from 8-12-week-old WT mice were isolated by crushing compact bone and cells were lineage depleted by magnetic separation (Miltenyi Biotec). c-kit$^+$ BM cells were pre-stimulated for 24 hours in CellGro media (Corning) supplemented by murine stem-cell factor (m-Scf, 50 ng/ml, Peprotech) and murine thrombopoietin (m-Tpo, 50 ng/ml, Peprotech). Oncoretroviral vectors were pseudotyped with ecotropic envelope and produced using standard protocols. Retroviral transduction was performed on retroNectin (Takara Bio)-coated cell culture dishes loaded with unconcentrated virus. Cells were resuspended in virus containing medium in the presence of 4 μg/ml polybrene at 37° C. for a minimum of 24 hours. Lentiviral particles were produced by transient transfection with lentiviral plasmid together with pSPAX and VSVG packaging plasmids using Fugene. Lentivirus and retrovirus particles were concentrated by ultracentrifugation at 4° C.

Isolation of Bone Marrow Stromal Cells for scRNA Sequencing

After sacrifice bones (femurs, hip, spine) were crushed in PBS/10% FCS on ice. The cells were dissociated by filtering through a 70 μm nylon mesh. For magnetic activated cell sorting cells were incubated with biotinylated antibodies directed against lineages (CD11b, GR1, NK1.1, TER119, CD4, CD8 and B220), CD45, CD71 and CD41 (biolegend; 6 μg/ml/1e7 cells) for 10 minutes. After centrifugation for 5 minutes at 300×g and 4°, cells were resuspended in 80 μl/1e7 cells PBS/10% FCS, mixed with 20 μl/1e7 cells magnetic anti-biotin beads (Biolegend) and incubated for 15 minutes at 4° C. with gentle agitation. For magnetic depletion, cells were resuspended in 1 ml PBS/10% FCS and placed into a cell separation magnet (BD) for 15 minutes at 4° C. For additional purification, the negative fraction was transferred to a new FACS-tube and placed into the cell separation magnet for another 30 minutes. The supernatant was centrifuged for 5 minutes at 300×g at 4° C.

FACS-Staining and Sorting of Bone Marrow Stromal Cells for scRNA Sequencing

Cells were resuspended in 300 μl PBS/2% FCS and stained at 4° C. for 20 minutes. Washing was performed by adding 1 ml PBS/2% FCS and centrifuging for 5 minutes at 300×g, 4° C. After resuspension and addition of Hoechst (1:10000), lineage/CD45/Ter119 negative cells were sorted into 50 μl DMEM/10% FCS (BD Aria III). Unstained cells were used as negative controls to define gating. All antibodies were acquired from Biolegend. The following fluorochrome conjugated antibodies were used: CD41-APC-Cy7, CD3-APC-Cy7, CD11b-APC-Cy7, Gr1-APC-Cy7, Ten 19 -APC-Cy7, B220-APC-Cy7, CD45.1-APC-Cy7, CD45.2-APC-Cy7, Sca1-PerCP, CD31-APC, CD51-PE.

Single Cell Library Preparation and Sequencing

The libraries were prepared using the Chromium Single Cell 3' Reagent Kits (v2): Single Cell 3' Library & Gel Bead Kit v2 (PN-120237), Chromium Single Cell A Chip Kit v2 (PN-120236) and i7 Multiplex Kit (PN-120262) (10×Genomics), and following the Single Cell 3' Reagent Kits (v2) User Guide (manual part no. CG00052, Rev D). Finalized libraries were sequenced on a Novaseq6000 platform (Illumina), aiming for a minimum of 50.000 reads/cell using the 10×Genomics recommended number of cycles (28-8-0-91 cycles).

Single Cell RNA Seq Data Analysis

We use cellranger (version 2.1.1) to align reads to mouse genome mm10 and for detection of cells with default parameters. Next, we used Seurat (v2.3.4, v3.1.0) for high level analysis of the scRNA-seq (Satija, R. et al. (2015), Nature biotechnology, 33(5), pp. 495-502). We filtered cells only keeping ones with low amount of mitochondrial genes (<0.03), low amount of ribosomal genes (<0.6). We removed cells with more than 30.000 UMIs as they represent potential duplets. Finally, we filtered genes detected in less than 30 cells. Next, we regressed out cell cycle, the proportion of mitochondrial, ribosomal and UMI counts and performed a log-normalization of read counts using Seurat. Data of ThPO (or Jak2) experiments were then integrated with a canonical correlation analysis (CCA) based on the first 15 CCs (Butler et al, supra). Next, we performed a clustering with a SNN of k=15 and produced a t-SNE representation with perplexity set as 75. Differential gene expression analysis was performed with Seurat to find cluster specific genes or genes changing between distinct phenotypes.

GO and pathway enrichment analysis were based on clusterProfiler (Version 3.12.0; Yu, G. et al. (2012), Omics: a journal of integrative biology, 16(5), pp. 284-287) and CAMERA from edgR (Version 3.26.7; McCarthy, D. J., Chen, Y. and Smyth, G. K. (2012), Nucleic acids research, 40(10), pp. 4288-4297). We have also proposed gene sets describing "hematopoiesis-support", "MSC progenitor phenotype", "non-collagenous ECM" and "collagenous ECM". Pre-ranked GSEA analysis was performed as described (Version 4.0; Subramanian, A. et al. (2005) 'Gene set enrichment analysis: a knowledge-based approach for interpreting genome-wide expression profiles', Proceedings of the National Academy of Sciences of the United States of America, 102(43), pp. 15545-15550). All P-values were corrected by Benjamini-Hochberg correction.

Quantification of S100A8 in Human Plasma Samples

Patient samples were collected and supplied by the University Clinic Hamburg-Eppendorf (UKE); University Hospital RWTH Aachen and University. Samples were deidentified at the time of inclusion. All patients provided informed consent and the data collection was performed in accordance with the Declaration of Helsinki. Control plasma was obtained from the Institute for Clinical Chemistry at Erasmus Medical Center in Rotterdam. Surplus material was collected from dermatological and cardiological patients after diagnostics according to the ethical vote MEC-2018-1445 and processed on the day of acquisition. All subjects had no history or indication of any hematological or non-hematological malignancy. Plasma was isolated from whole blood anticoagulated with EDTA by centrifugation (2000×g, 7 minutes) and stored at −80° C. Samples were thawed gently on ice and centrifuged for 5 minutes at 2500×g before further processing. Samples were diluted 1:100 and S100A8 concentration was quantified using the Human S100A8 DuoSet ELISA (R&D Systems, DY4570-05) according to the manufacturer's instructions.

Histological and Immunohistological Analysis

Murine organs were fixed in 4% paraformaldehyde for 24 hours and transferred to 70% ethanol. Femurs were decalcified in 10% EDTA/Tris-HCl (pH 6.6) solution for 72 hours, dehydrated and paraffin embedded. H&E and reticulin staining were performed on 4 μm sections according to established routine protocols.

Human bone marrow biopsies from the patients whose plasma was used for S100A8 quantification in plasma were chosen for histological examination from archived patient samples of paraffin-embedded tissue from the Biobank of Dr. G. Büsche at the Department of Pathology, Hannover Medical School, Hannover, Germany. Biopsies were primarily taken during earlier hospitalization. Bone marrow biopsies were fixed for 24 hours using the Hannover Solution (12% buffered formaldehyde plus 64% methanol), decalcified (EDTA), dehydrated and embedded in paraffin. Control bone marrow slides were acquired from the Department of Pathology at Erasmus Medical Center. All reference patients showed normal bone marrow characteristics and had evidence for or history of hematological malignancies.

For immunohistochemical analysis of S100A8, antigen retrieval was performed using citrate buffer in a conventional lab microwave (Vector, antigen unmasking solution). Sections were treated with 3% $H_2O_2$ and blocked with Avidin/Biotin blocking kit (Vector), and subsequently incubated with primary antibody (rabbit-anti-S100A8: ab92231 (Abcam), 1:200; rabbit-anti-CD56: RBK050 (Zytomed Systems), 1:100) for one hour at room temperature. Biotinylated monoclonal goat anti-rabbit-antibody (Vector) was used as a secondary antibody for 30 minutes at room temperature. Slides were incubated with AB complex for 30 minutes at room temperature, washed and incubated for a further 10 minutes with DAB substrate. Slides were stained with hematoxylin and mounted with glass coverslip using DPX mountant (Sigma).

Statistical Analysis

Statistical analysis—excluding that for single cell RNAseq Data—was conducted using either GraphPad Prism Version or R Version 3.6.1. Data are presented as mean±SEM. Two independent groups with (approximately) normally distributed samples were compared with an unpaired t-test. When normality could not be assumed, Wilcoxon Rank Sum test was used. For ≥2 groups, ANOVA was employed with post-hoc paired t-test and Bonferroni correction for multiple hypothesis testing.

Mice

For JAK2V617F studies, WT BM cells were transduced with JAK2(V617F) (JAK2) retrovirus or control pMIG retrovirus (control: JAK2 empty vector) and transplanted into 10.5 Gy-irradiated 8-10-week-old female B6.SJL recipients. Mice were randomly assigned to transplant groups. Mice from the early ThPO cohort were sacrificed 5 weeks post-transplant, whilst mice in the late ThPO cohort were sacrificed 10 weeks post-transplant. Mice used in the JAK2 experiment were sacrificed at 28 weeks post-BM transplant, when hemoglobin levels decreased, owing to the varying phenotypic severity of JAK2V617F.

Blood was periodically collected from mice via submandibular bleeds into Microtainer tubes coated with $K_2$EDTA (Becton Dickinson, NJ, USA) and complete blood counts were performed on a Horiba Scil Vet abc Plus hematology system.

Mouse Transplants

For tasquinimod studies, WT recipient mice (n=7-10/group) were lethally irradiated (10.5 Gy) and received ckit$^+$ cells transduced with JAK2$^{(V671F)}$- or JAK2$^{(WT)}$ retroviral virus. Tasquinimod treatment (ABR-215050, Biorbyt) was administered via drinking water at 30 mg/kg/day dissolved in 3% sucrose in autoclaved water. Tasquinimod was first dissolved in DMSO and mixed with 3% sucrose, 2% PEG300 (Sigma) in water. Vehicle-treated groups received DMSO-, PEG300-treated water with 3% sucrose. Drinking bottles were renewed twice a week. Treatment was started at 5 weeks post-transplant until 10 post-transplant, and resumed at 13 weeks post-transplant until sacrifice at 20 weeks post-transplant. Mice were randomly assigned to transplant and treatment groups.

Results

Figure 1D:
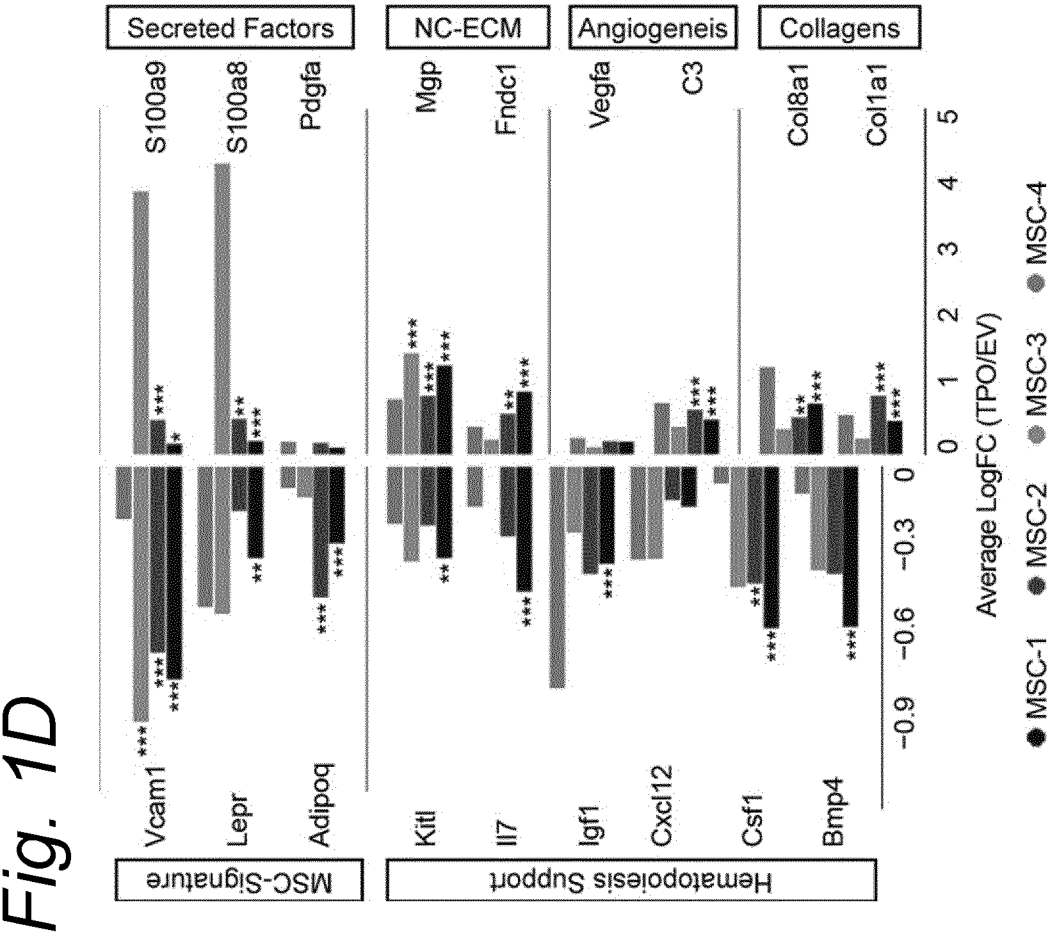
Figure 1C:
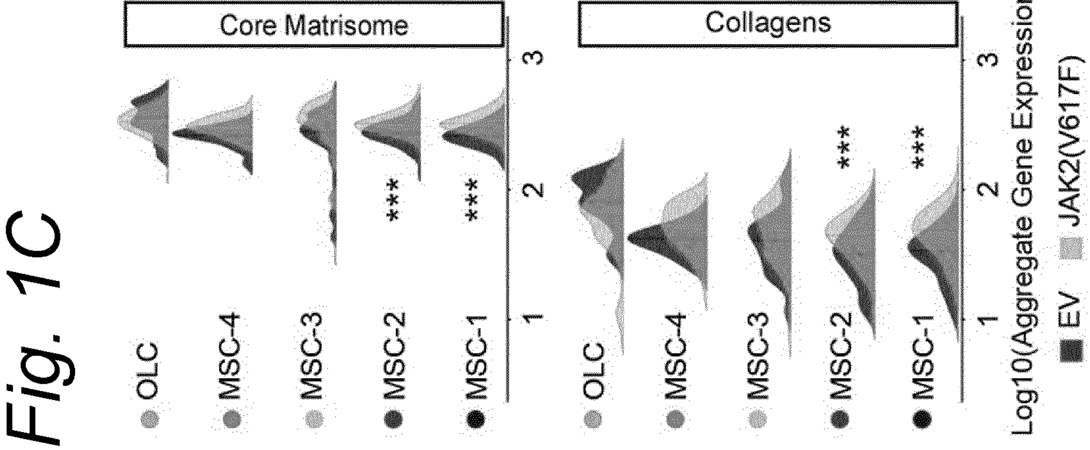

Single Cells Analysis of the Bone Marrow Microenvironment Confirms MSC-1 and -2 as Fibrosis-Driving Cells The JAK2V617F mutation is found in the majority (50-60%) of patients with PMF. The retroviral expression of the JAK2V617F mutation in transplanted HSPCs leads to an MPN phenotype including splenomegaly due to extramedullary hematopoiesis and the development of myelofibrosis after a short latency with a high degree of penetrance (Mullally, A. et al. (2012), Hematology/oncology clinics of North America, 26(5), pp. 1065-1081; Schneider, R. K. et al. (2017), Cell stem cell, 20(6), pp. 785-800.e8). The inventors thus either transplanted c-kit$^+$ HSCPs expressing the JAK2V617F mutation or the control empty vector (EV) into lethally irradiated mice. Around 24 weeks after transplantation, bone marrow histology demonstrated severe fibrosis, characterized by thick, intercrossing reticulin-positive fibers and also severe osteosclerosis, indicative of grade 3 myelofibrosis (FIG. 1A). Unsupervised clustering of 1292 high quality non-hematopoietic niche cells lead to the identification of 8 distinct clusters/populations (FIG. 1B): 1-4) clusters of mesenchymal stromal cells (MSC-1: adipogenic, MSC-2: osteogenic, MSC-3: transition, MSC-4: interferon high), 5) and 6) clusters of Schwann cell precursors (SCPs; 1: non-myelinating SCPs, nmSCPs; 2: myelinating SCPs, mSCPs), 7) osteoblastic lineage cells (OLCs) and 8) arterial cells (ACs). MSC-1 and MSC-2 showed the highest up-regulation of extracellular matrix (ECM) proteins, in particular "core matrisome" and collagens, confirming that these two MSC populations are the cellular drivers of the fibrotic progression and acquire myofibroblast characteristics in fibrosis (FIG. 1C). The most significantly de-regulated genes in MSCs could be grouped into 1) down-regulated genes and 2) up-regulated genes with onset of the MPN phenotype (FIG. 1D). The down-regulated genes comprised 1) MSC markers (Vcam, Lepr, Adipoq) and 2) hematopoiesis-support (KitI, II7, Igf1, Cxcl12, Csf1, Bmp4). In particular MSC-1 showed a highly significant down-regulation of MSC markers and genes involved in the regulation of hematopoietic stem cells. A significant down-regulation of Vcam1 occurred in MSC-1, MSC-2 and -3, further indicating a spatial activation and migration of MSC as VCAM1 plays a central role in the firm adhesion of MSC to the ECM. The up-regulated genes were defined through four major biological processes: 1) secreted factors (S100a8, S100a9, Pdgfa), 2) osteogenesis (Mgp, Fndc1), 3) neoangiogenesis (Vegfa, C3) and 4) ECM synthesis (Col8a1, Col1a1). Interestingly, among the secreted factors the alarmins S100a8/S100a9, danger-associated molecular patterns (DAMPs)—known contributors to inflammatory responses—were significantly up-regulated in their expression in MSC-1 and -2, the subpopulations showing the most significant changes.

Single Cells Analysis of the Bone Marrow Microenvironment in Patients with Primary Myelofibrosis (PMF/MPN) Confirms MSC as Fibrosis-Driving Cells and Up-Regulation of S100A8/S100A9

Figure 2A:
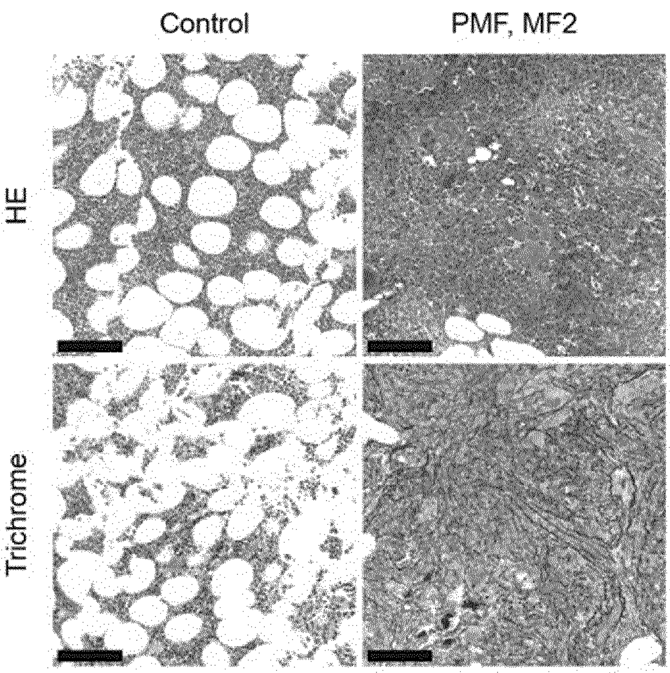
Figure 2B:
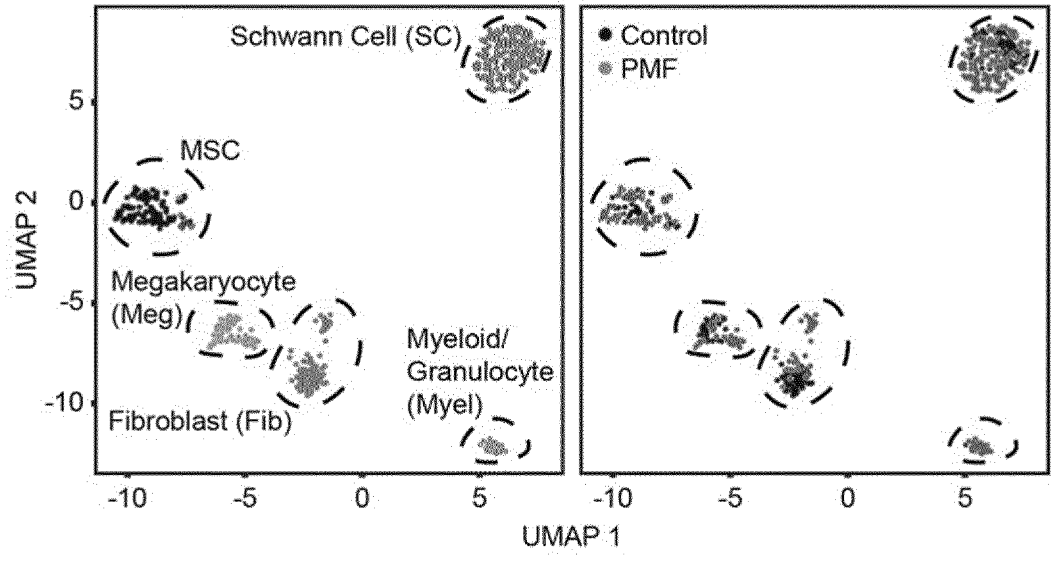
Figure 2C:
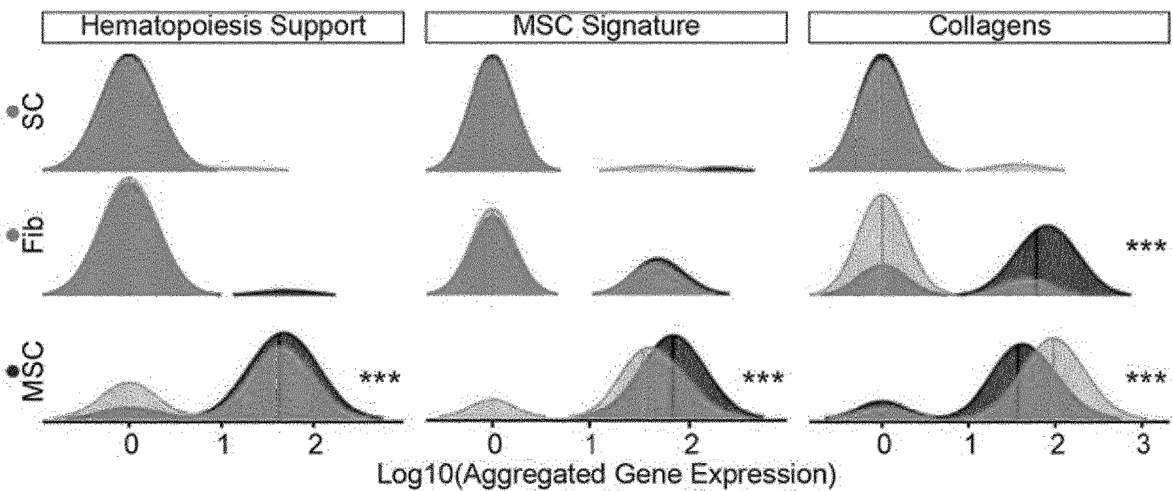
Figure 2D:
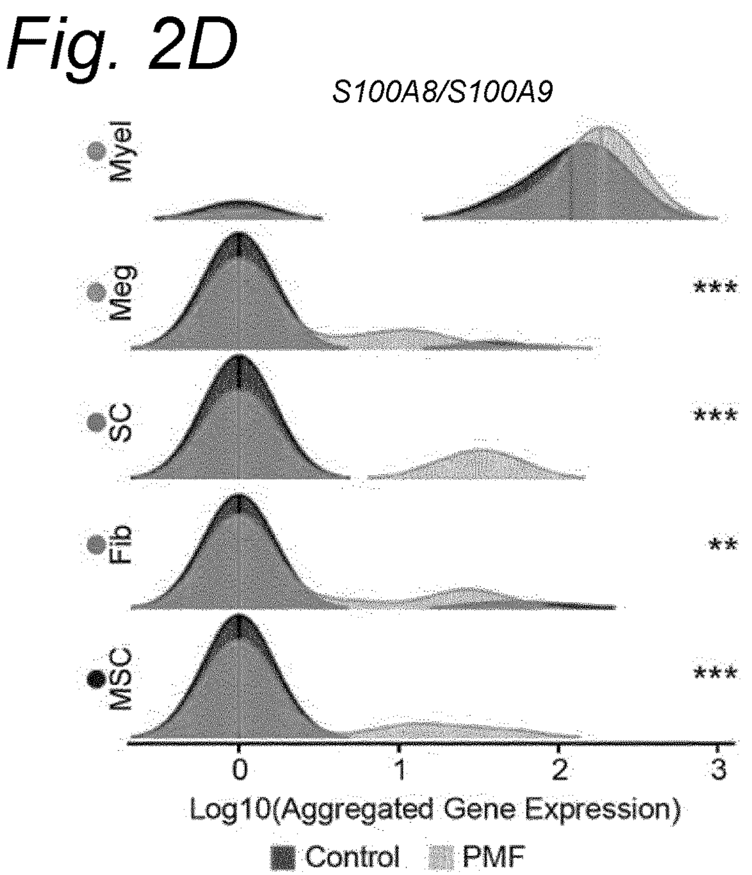
Figure 2E:
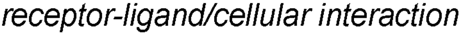
Figure 2E:
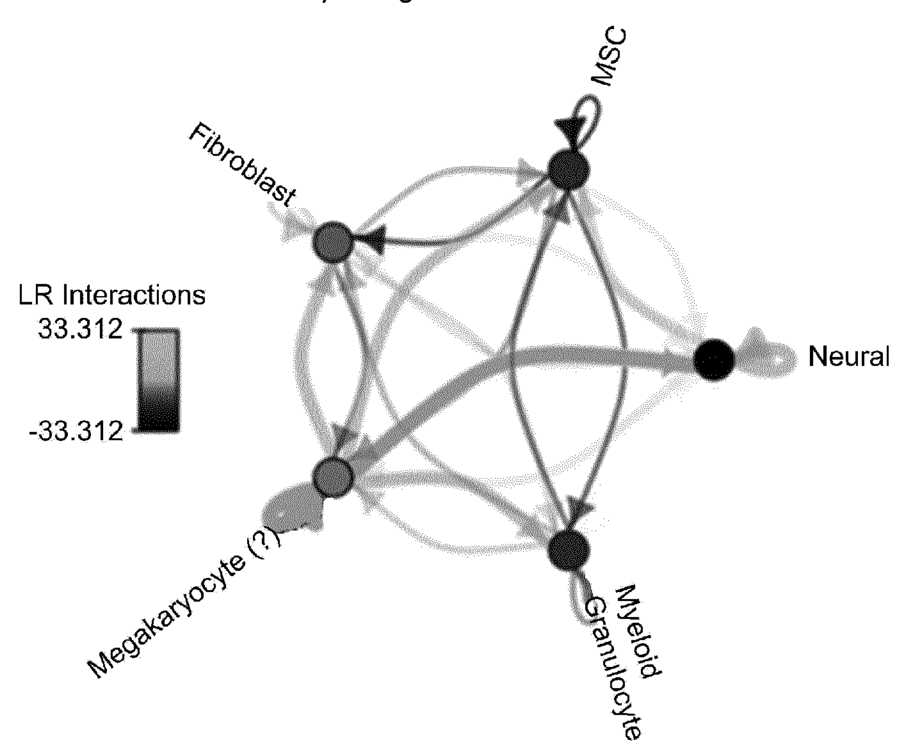
Figure 2E:
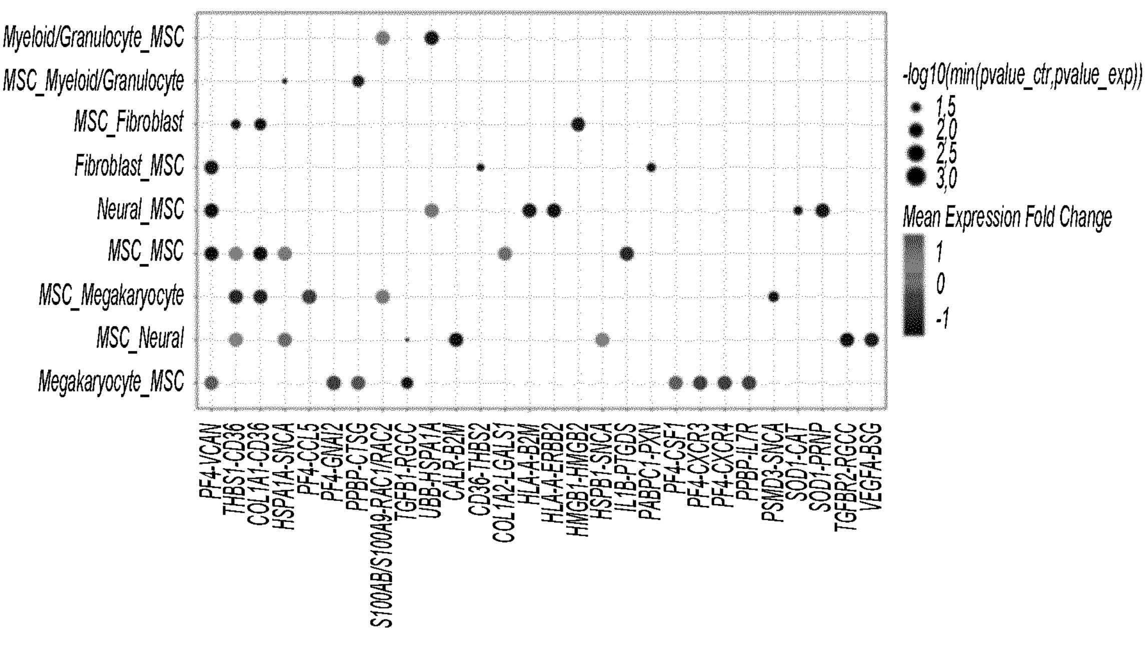

The inventors aimed to validate the findings of transcriptional changes in the bone marrow microenvironment in patient bone marrow biopsies. Single cells of the bone marrow microenvironment were isolated from a PMF patient with grade 2 (advanced) myelofibrosis from a small piece of a bone marrow punch biopsy and from two age-matched control patients with peripheral lymphoma without contribution to the bone marrow. The HE analysis of the bone marrow showed a hypercellular marrow in the PMF patient with dysplastic megakaryocytes and thick coarse black fibers in the Reticulin staining (FIG. 2A). In contrast, control patients showed a normocellular bone marrow without any fibers present. Unsupervised clustering of high-quality non-hematopoietic niche cells lead to the identification of 5 distinct clusters/populations (FIG. 2B): 1) mesenchymal stromal cells (MSCs), 2) megakaryocytes (Meg), 3) fibroblasts (Fib), 4) myeloid/granulocyte (myel) and 5) Schwann Cells (SCs). Exactly as seen in the murine model of PMF/MPN MSCs were functionally reprogrammed, lost their hematopoiesis support (support of normal blood formation) and MSC signature and were the fibrosis-driving cells, significantly up-regulating Collagens (FIG. 2C). Interestingly, and again exactly as seen in the murine model, MSC, that usually do not express S100A8/S100A9 at all, showed strong up-regulation of S100A8/S100A9 (FIG. 2D). This indicates that the up-regulation of S100A8/S100A9 is a disease-specific/MPN-specific mechanisms that can be both a disease marker and a therapeutic target. Looking into the interaction of S100A8 with downstream receptors, it became obvious, that mainly the interaction with RAC1/RAC2 increased (FIG. 2E).

S100A8 as a Biomarker for Disease Progression/Fibrosis Onset in MPN

The inventors asked if S100A8 might serve as a marker for progression of (human) bone marrow fibrosis as they also observed increased S100a8/S100a9 expression in murine models in MSCs already in pre-fibrosis (compared to control) which then significantly increased in fibrotic stages in almost all niche cells, suggesting S100A8 as a sensitive marker for disease/fibrosis progression.

Figure 3A:
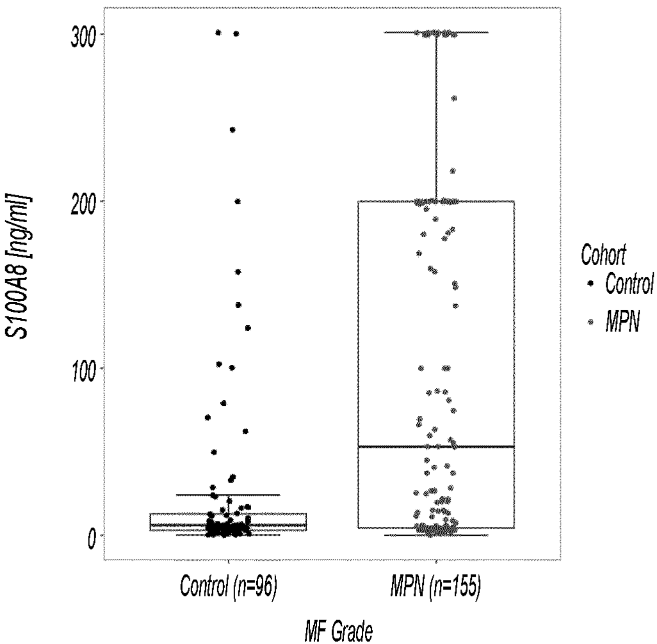
Figure 3B:
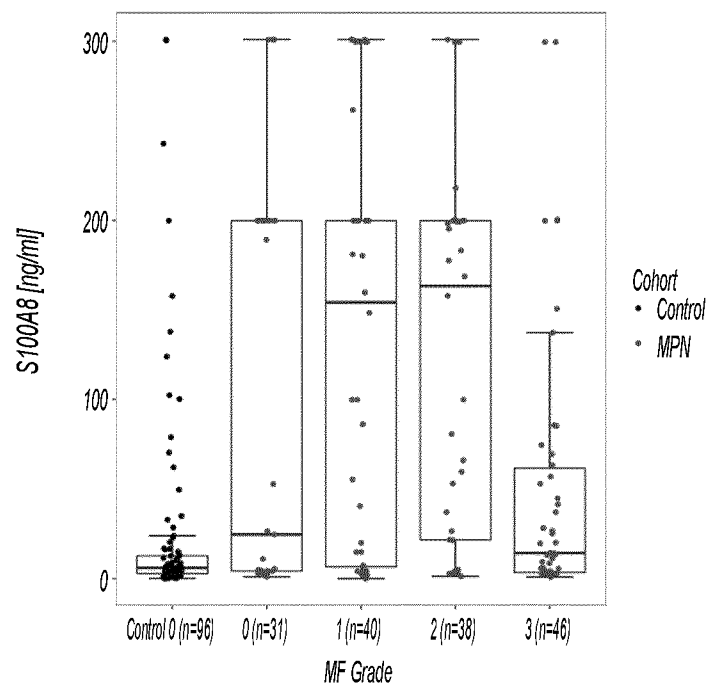

The inventors therefore quantified S100A8 in plasma samples (peripheral blood) from MPN patients (n=155) and age-matched patients without a primary hematological disease (n=96) by ELISA. S100A8 was significantly increased in MPN patients (FIG. 3A) and clearly demarcated the transition from MF0 to MF1 and higher MF grades in general, indicating S100A8 as a sensitive biomarker for fibrosis onset or progression in PMF (when follow-up samples are taken; FIG. 3B). In previous work, the inventors linked increased S100A8 expression in the stroma (in MDS) to decreased hematopoiesis-support (Ribezzo, F. et al. (2019), Leukemia, 33(7), pp. 1759-1772), underlining that S100A8 is a good marker for the reprogramming of the stroma from hematopoiesis-support towards fibrotic transformation, in particular if followed up in patients over time.

Figure 3C:
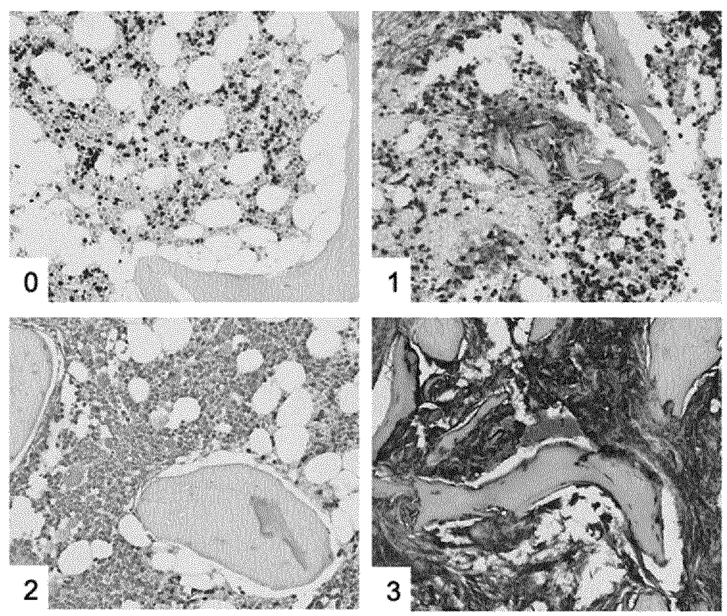
Figure 3D:
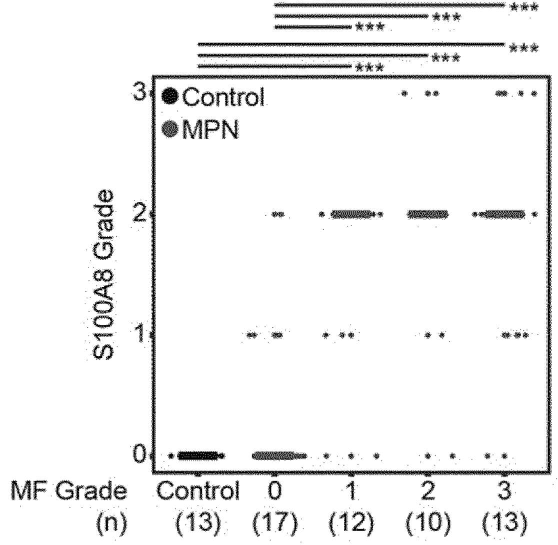

The inventors further performed immunohistochemistry for S100A8 in bone marrow biopsies from patients and controls (FIG. 3C). In control bone marrow biopsies (MF0), S100A8 specifically marks neutrophils (S100A8 grade 0). Already in low grades of fibrosis, S100A8 is not only expressed in hematopoietic cells but stains positive in the interstitium (grade 1-2), while in progressed fibrosis (MF3) stromal cells are strongly positively stained (grade 3). The quantification of the S100A8 score showed that it correlates with disease severity reflected by the MF grade (FIG. 3D).

Figure 4A:
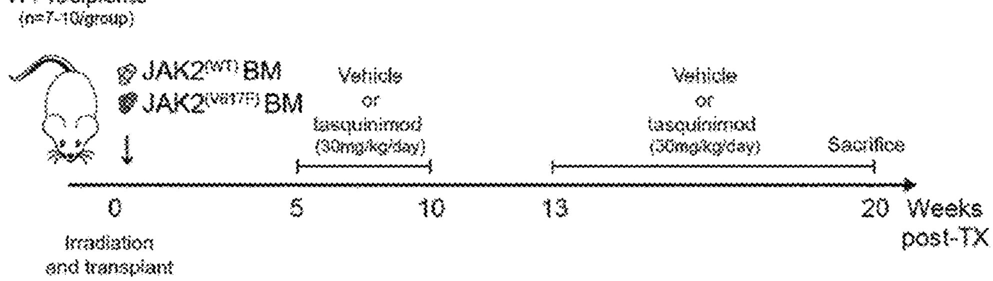

Tasquinimod as an Inhibitor of S100A8/S100A9 Ameliorates the MPN Phenotype and Bone Marrow Fibrosis To further validate the role of S100A8/S100A9 in the fibrotic initiation and progression, the inventors sought to use a S100A9-inhibitor known as tasquinimod (ABR-215050) in mice developing JAK2(V617F)-mediated myelofibrosis. Tasquinimod, a quinoline compound with anti-angiogenic and anti-tumor activity under investigation for solid tumors (Isaacs et al., 2006, supra), binds to S100A9 protein and impedes its interaction with TLR4 and RAGE receptors. Tasquinimod treatment was administered via drinking water starting at 5 weeks post-transplant, until sacrifice at 20 weeks post-transplant with a treatment break at 10 weeks post-transplant to minimize deleterious effects on normal granulocyte function (FIG. 4A).

Figure 4B:
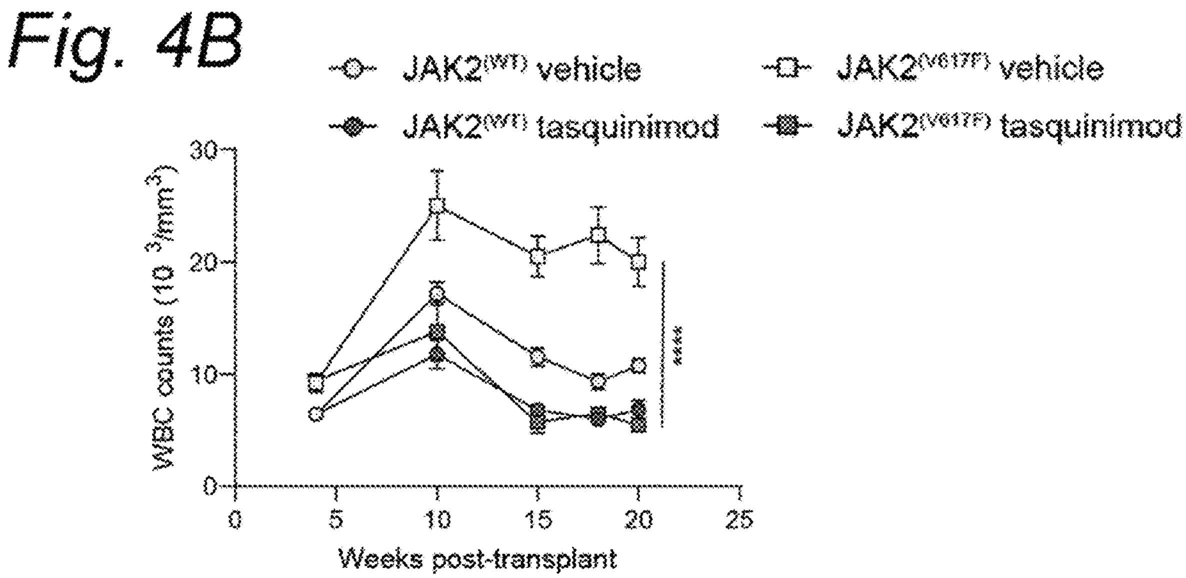
Figure 4C:
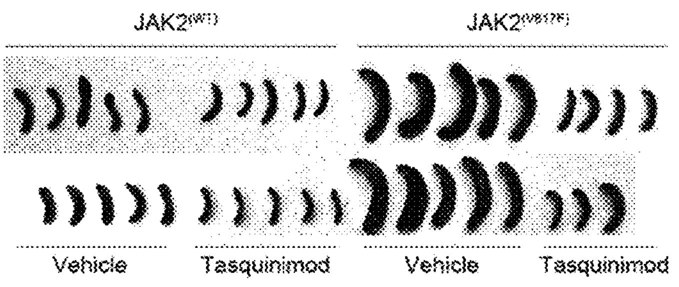
Figure 4D:
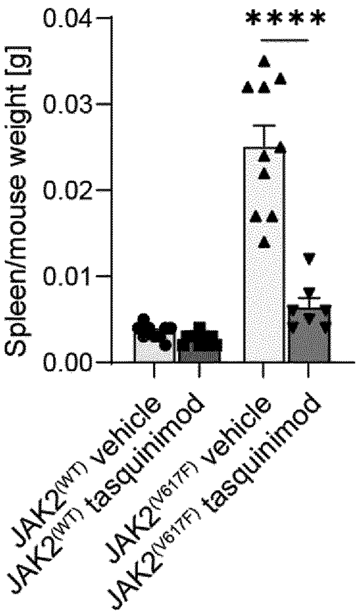

Crucially, JAK2$^{(V617F)}$ mice receiving tasquinimod did not develop MPN-specific leukocytosis, which was observed in the JAK2$^{(V617F)}$-vehicle-treated mice (FIG. 4B). Severe splenomegaly, which is a major clinical manifestation in PMF patients, was observed in vehicle-treated JAK2 (V617F) mice but completely normalized with tasquinimod treatment (FIG. 4C-D).

Figure 4E:
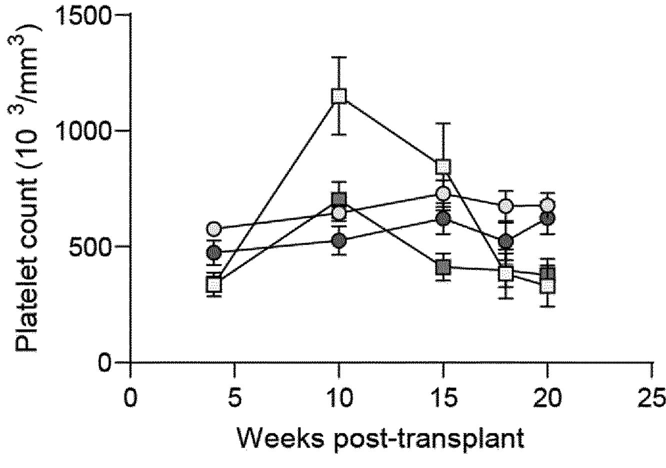
Figure 4F:
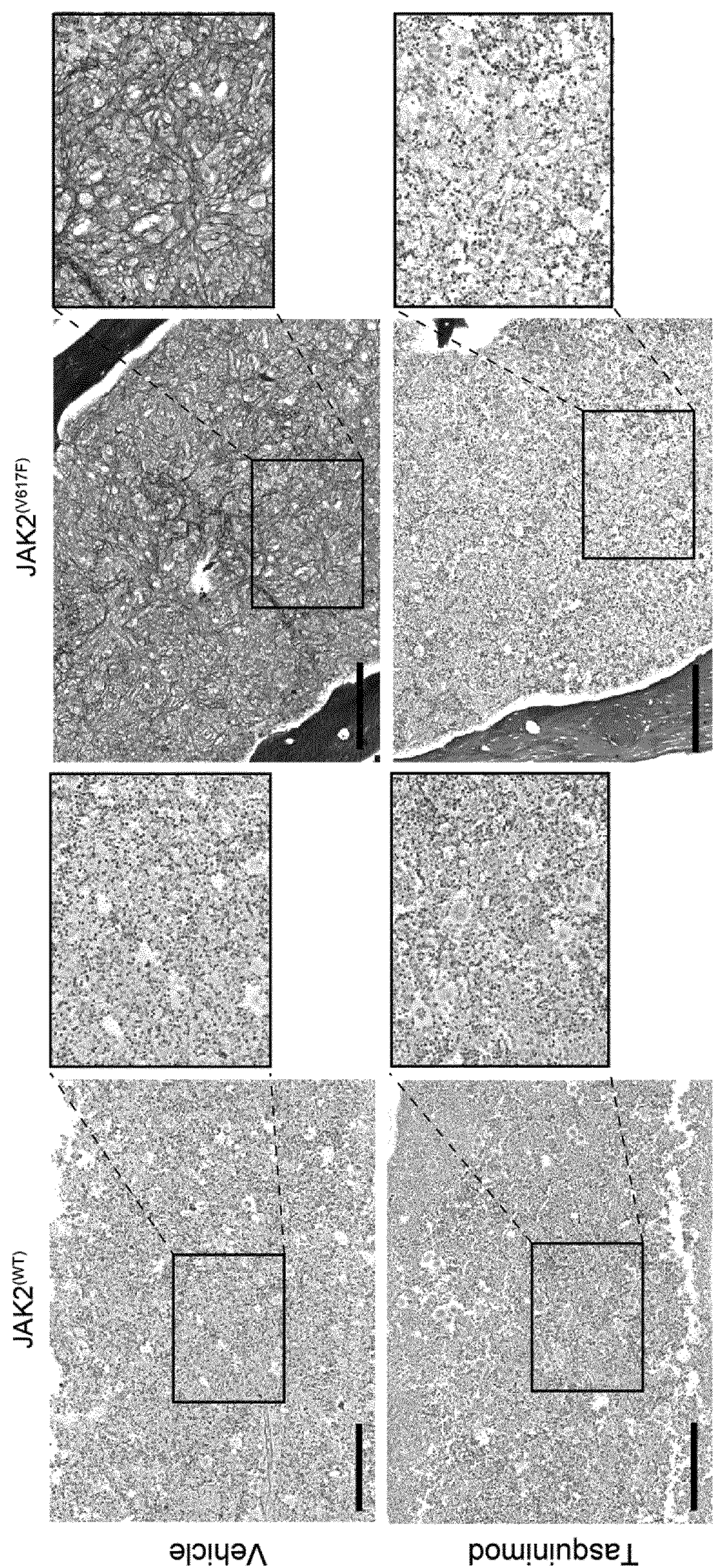
Figure 4G:
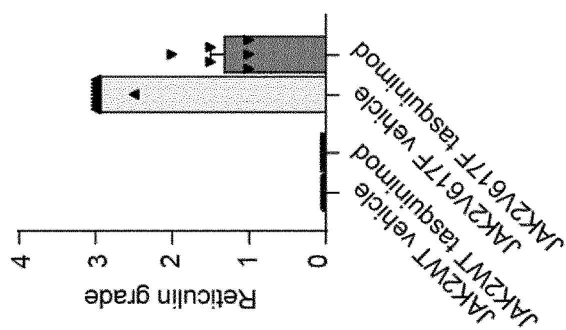
Figure 4H:
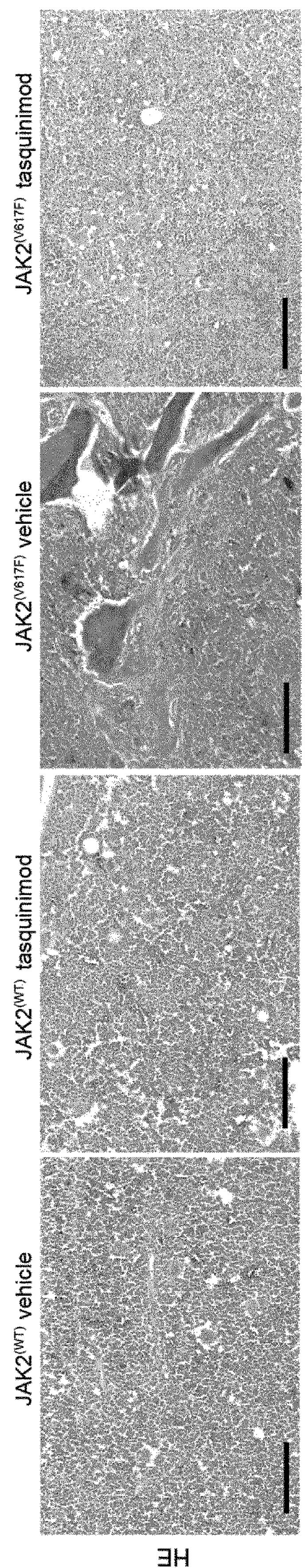

The inventors observed a progressive increase in peripheral platelet counts until 10 weeks post-transplant in JAK2$^{(V617F)}$ mice, followed by a sharp decrease in platelets associated with the progressive replacement of hematopoietic cells in the bone marrow (FIG. 4E).

Critically, JAK2$^{(V617F)}$ mice treated with tasquinimod did not develop thrombocytosis. Additionally, tasquinimod treatment in JAK2$^{(V617F)}$ mice reduced fibrosis grade, compared to JAK2$^{(V617F)}$-vehicle-treated mice that developed grade 2-3 fibrosis and osteosclerosis (FIG. 4F-H), indeed showing that the inhibition of S100A8/S100A9 through Tasquinimod has a striking effect on reduction of life-threatening symptoms in patients with MPN/PMF.

CONCLUSIONS

- S100A8/S100A9 are significantly up-regulated in the plasma of patients with MPN
- S100A8/S100A9 is up-regulated in fibrosis-driving cells in MPN/PMF
- The up-regulation of S100A8/S100A9 in the plasma of patients marks the progression of MPN into a fibrotic phenotype/disease progression
- Kinetics of S100A8/S100A9 in MPN patients can be used to track the disease course in a patient
- S100A8/S100A9 are an attractive therapeutic target in MPN
- Tasquinimod ameliorates the MPN phenotype and inhibits bone marrow fibrosis and splenomegaly as life-threatening symptoms in patients

The invention claimed is:

1. A method of treatment, comprising administering an inhibitor of a S100 protein to a mammal that has myelofibrosis, wherein the inhibitor is a compound of formula (I)

(I)

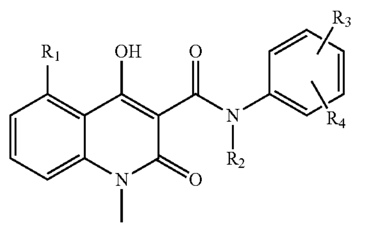

or a pharmaceutically acceptable salt thereof, wherein $R_1$ is selected from the group consisting of H, methyl, ethyl, n-propyl, iso-propyl, methoxy, ethoxy, fluoro, chloro, bromo, trifluoromethyl, and trifluoromethoxy;

$R_2$ is C1-C4 alkyl;

$R_3$ is selected from the group consisting of methyl, methoxy, hydrogen, fluoro, chloro, bromo, trifluoromethyl, and trifluoromethoxy; and $R_4$ is selected from the group consisting of hydrogen, fluoro and chloro, with the proviso that $R_4$ is selected from fluoro and chloro only when $R_3$ is selected from fluoro and chloro.

2. The method according to claim 1, wherein administering the inhibitor to the mammal reduces the progression of the myelofibrosis.

3. The method according to claim 1, wherein the S100 protein is at least one of S100A8 and S100A9.

4. The method according to claim 1, wherein $R_2$ is methyl or ethyl.

5. The method according to claim 1, wherein $R_3$ is in para-position.

6. The method according to claim 1, wherein $R_3$ is selected from the group consisting of hydrogen, and trifluoromethyl.

7. The method according to claim 1, wherein $R_3$ is trifluoromethyl.

8. The method according to claim 1, wherein $R_4$ is hydrogen.

9. The method according to claim 1, wherein the inhibitor is 4-hydroxy-5-methoxy-N,1-dimethyl-2-oxo-N-[4-(trifluoromethyl)phenyl]-1,2-dihydroquinoline-3-carboxamide or a pharmaceutically acceptable salt thereof.

10. The method according to claim 1, wherein the inhibitor is administered at a total daily dose of about 0.05-10 mg.

11. The method according to claim 1, wherein the inhibitor is administered orally.

12. The method according to claim 1, wherein the inhibitor is administered in combination with at least one of radiation therapy, chemotherapy, and stem cell transplantation.

13. The method according to claim 1, wherein the inhibitor is administered in combination with a JAK2 inhibitor.

* * * * *